(12) United States Patent
Siegal

(10) Patent No.: US 9,888,911 B2
(45) Date of Patent: Feb. 13, 2018

(54) SURGICAL IMPALING MEMBER

(71) Applicant: NLT SPINE LTD., Kfar Saba (IL)

(72) Inventor: Tzony Siegal, Moshav Shoeva (IL)

(73) Assignee: NLT SPINE LTD., Kfar Saba (IL)

( * ) Notice: Subject to any disclaimer, the term of this patent is extended or adjusted under 35 U.S.C. 154(b) by 468 days.

(21) Appl. No.: 14/390,036

(22) PCT Filed: May 28, 2013

(86) PCT No.: PCT/IB2013/054403
§ 371 (c)(1),
(2) Date: Oct. 2, 2014

(87) PCT Pub. No.: WO2013/179222
PCT Pub. Date: Dec. 5, 2013

(65) Prior Publication Data
US 2015/0073421 A1 Mar. 12, 2015

Related U.S. Application Data

(60) Provisional application No. 61/671,812, filed on Jul. 16, 2012, provisional application No. 61/652,247, filed on May 28, 2012.

(51) Int. Cl.
*A61B 17/04* (2006.01)
*A61B 17/02* (2006.01)
(Continued)

(52) U.S. Cl.
CPC ........ *A61B 17/025* (2013.01); *A61B 17/0218* (2013.01); *A61B 17/7055* (2013.01); *A61B 17/7076* (2013.01); *A61F 2/447* (2013.01); *A61F 2/4611* (2013.01); *A61B 17/8625* (2013.01); *A61B 2017/0256* (2013.01); *A61B 2017/0262* (2013.01); *A61F 2/442* (2013.01); *A61F 2002/2817* (2013.01); *A61F 2002/2835* (2013.01); *A61F 2002/30062* (2013.01); *A61F 2002/3085* (2013.01); *A61F 2002/30187* (2013.01); *A61F 2002/30212* (2013.01); *A61F 2002/30232* (2013.01);
(Continued)

(58) Field of Classification Search
CPC ..... A61B 17/84; A61B 17/844; A61B 17/864; A61B 17/8685; A61B 2017/8655
USPC ................................ 606/307, 313, 326–328
See application file for complete search history.

(56) References Cited

U.S. PATENT DOCUMENTS 4,013,071 A * 3/1977 Rosenberg ......... A61B 17/8685
411/397
5,139,511 A 8/1992 Gill
(Continued)

FOREIGN PATENT DOCUMENTS

EP  0077159  4/1983
EP  1844714  10/2007
(Continued)

*Primary Examiner* — Matthew Lawson
(74) *Attorney, Agent, or Firm* — Mark M. Friedman

(57) ABSTRACT

An implant for orthopedic surgery includes an impaling member (101,102), which is separable into portions (102a, 102b) for impaling and attaching to tissue, for example, bone. Once the portions (102a, 102b) of the impaling member (101,102) are separated and attached to the requisite tissue, they may accommodate stabilizing members for fixation, or other instrumentation for procedures such as fusion.

20 Claims, 26 Drawing Sheets

(51) Int. Cl.
*A61F 2/46* (2006.01)
*A61B 17/70* (2006.01)
*A61F 2/44* (2006.01)
*A61F 2/28* (2006.01)
*A61F 2/30* (2006.01)
*A61B 17/86* (2006.01)

(52) U.S. Cl.
CPC ............... *A61F 2002/30387* (2013.01); *A61F 2002/30579* (2013.01); *A61F 2002/30607* (2013.01); *A61F 2002/30616* (2013.01); *A61F 2002/30784* (2013.01); *A61F 2002/30904* (2013.01); *A61F 2002/30995* (2013.01); *A61F 2002/4415* (2013.01); *A61F 2002/4627* (2013.01); *A61F 2002/4628* (2013.01); *A61F 2002/4687* (2013.01); *A61F 2310/00017* (2013.01)

(56) References Cited

U.S. PATENT DOCUMENTS

| | | | |
|---|---|---|---|
| 5,489,210 A * | 2/1996 | Hanosh | A61C 8/0033 433/173 |
| 5,599,279 A | 2/1997 | Slotman et al. | |
| 6,419,705 B1 | 7/2002 | Erickson | |
| 6,613,053 B1 * | 9/2003 | Collins | A61B 17/7059 606/289 |
| 7,179,225 B2 | 2/2007 | SHiuzas et al. | |
| 2006/0217754 A1 | 9/2006 | Boehm et al. | |
| 2007/0073110 A1 | 3/2007 | Larson et al. | |
| 2007/0219416 A1 | 9/2007 | Perez-Cruet | |
| 2009/0024174 A1 * | 1/2009 | Stark | A61B 17/8625 606/321 |
| 2009/0099422 A1 | 4/2009 | George | |
| 2013/0041471 A1 | 2/2013 | Siegal et al. | |

FOREIGN PATENT DOCUMENTS

| | | |
|---|---|---|
| EP | 1935356 | 6/2008 |
| EP | 2412326 | 2/2012 |
| GB | 2240926 | 8/1991 |
| JP | 08-140988 | 6/1996 |
| JP | 2002532145 | 10/2002 |
| JP | 2002532145 | 7/2004 |
| JP | 2004530527 | 10/2004 |
| JP | 2004535215 | 11/2004 |
| JP | 2008532710 | 8/2008 |
| WO | 9834552 | 8/1998 |
| WO | 2009146252 | 12/2009 |
| WO | 2010052807 | 4/2013 |
| WO | 2013052807 | 4/2013 |

* cited by examiner

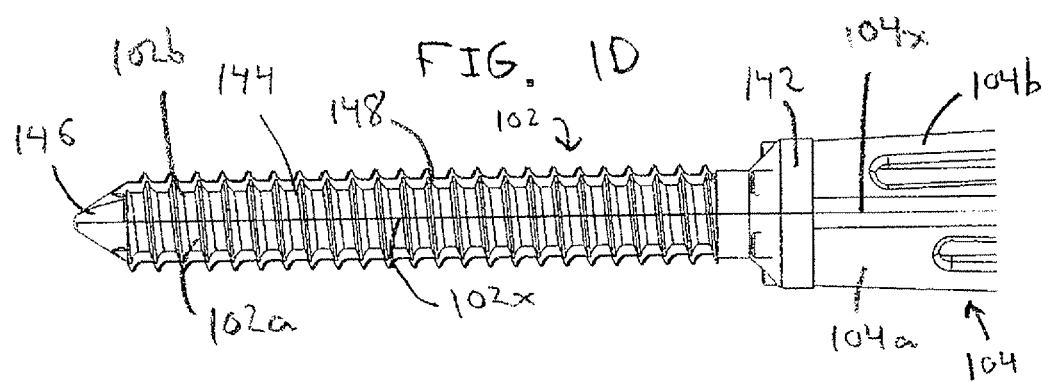
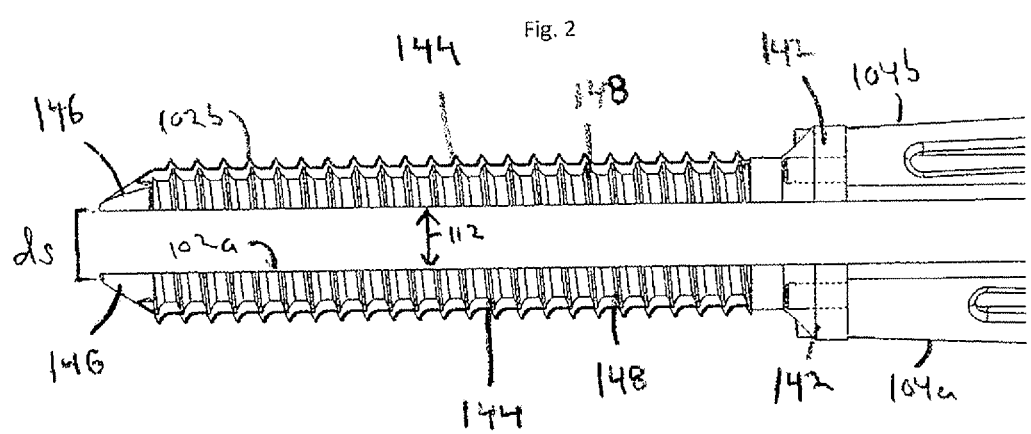

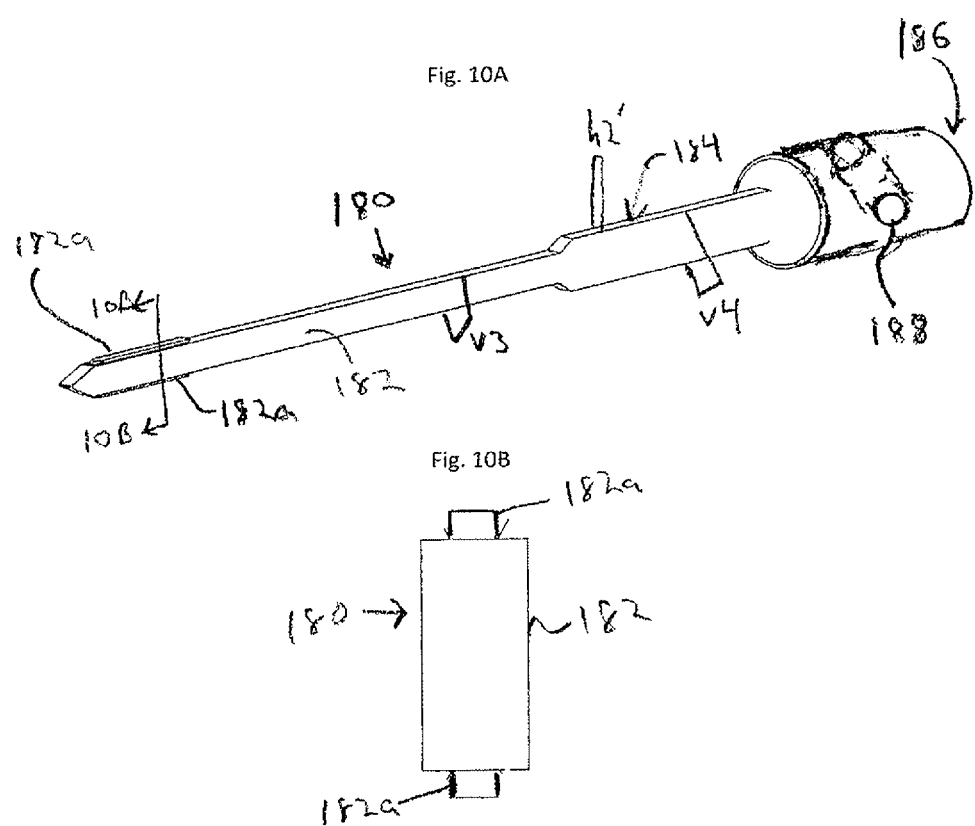

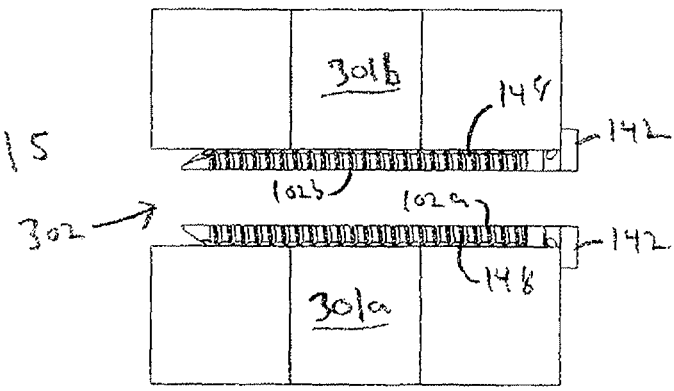
FIG. 15
Fig. 13
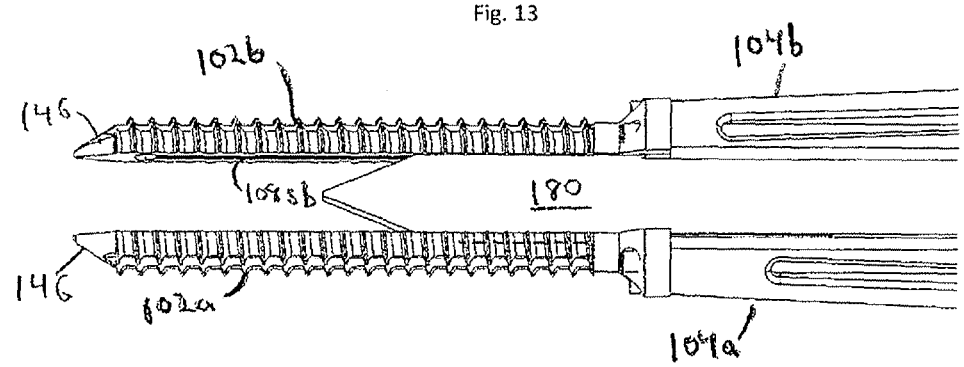
Fig. 14
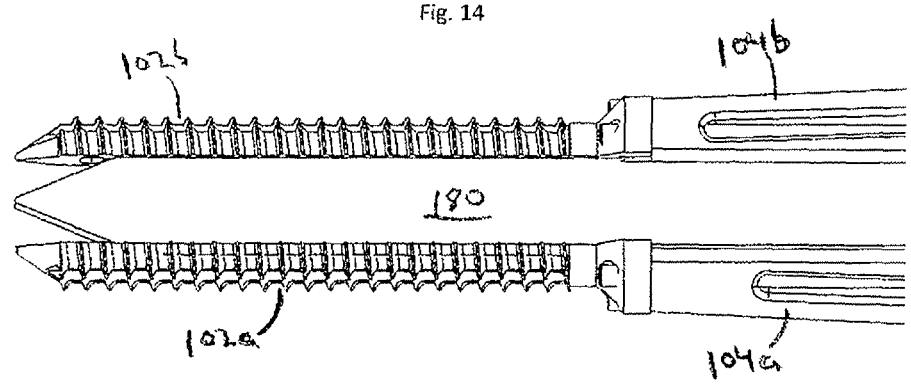

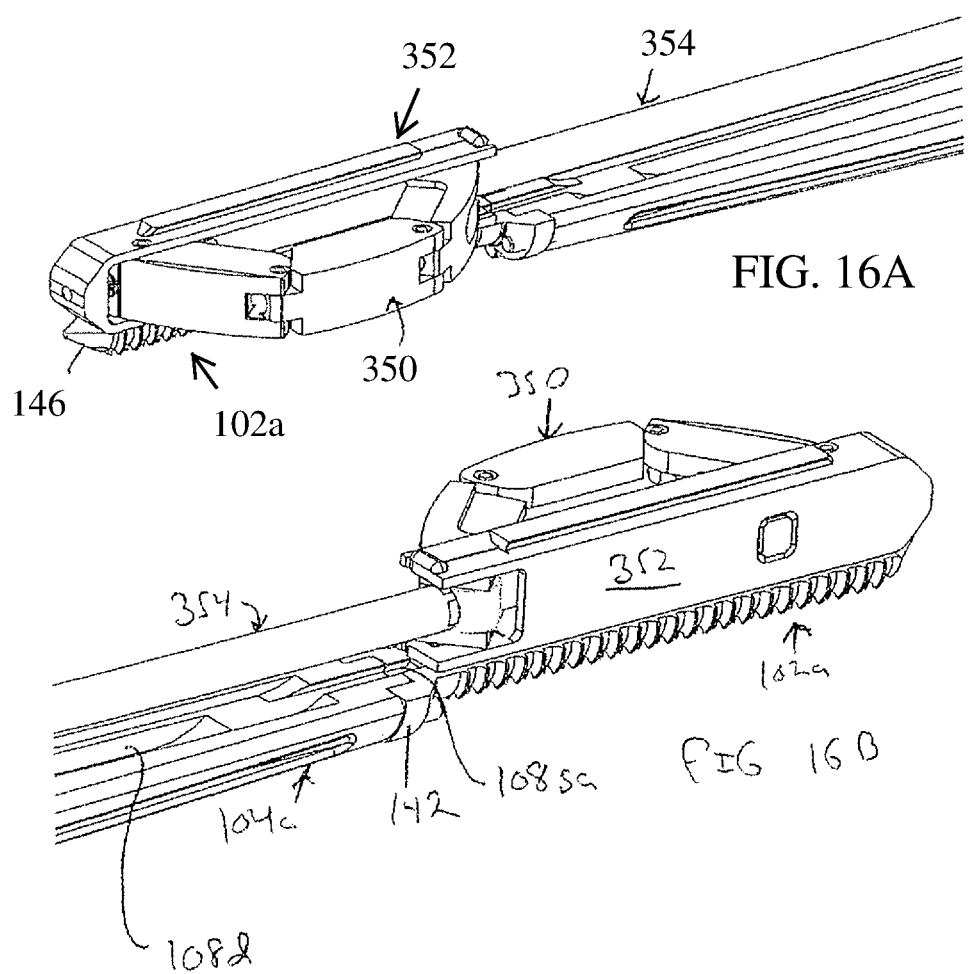

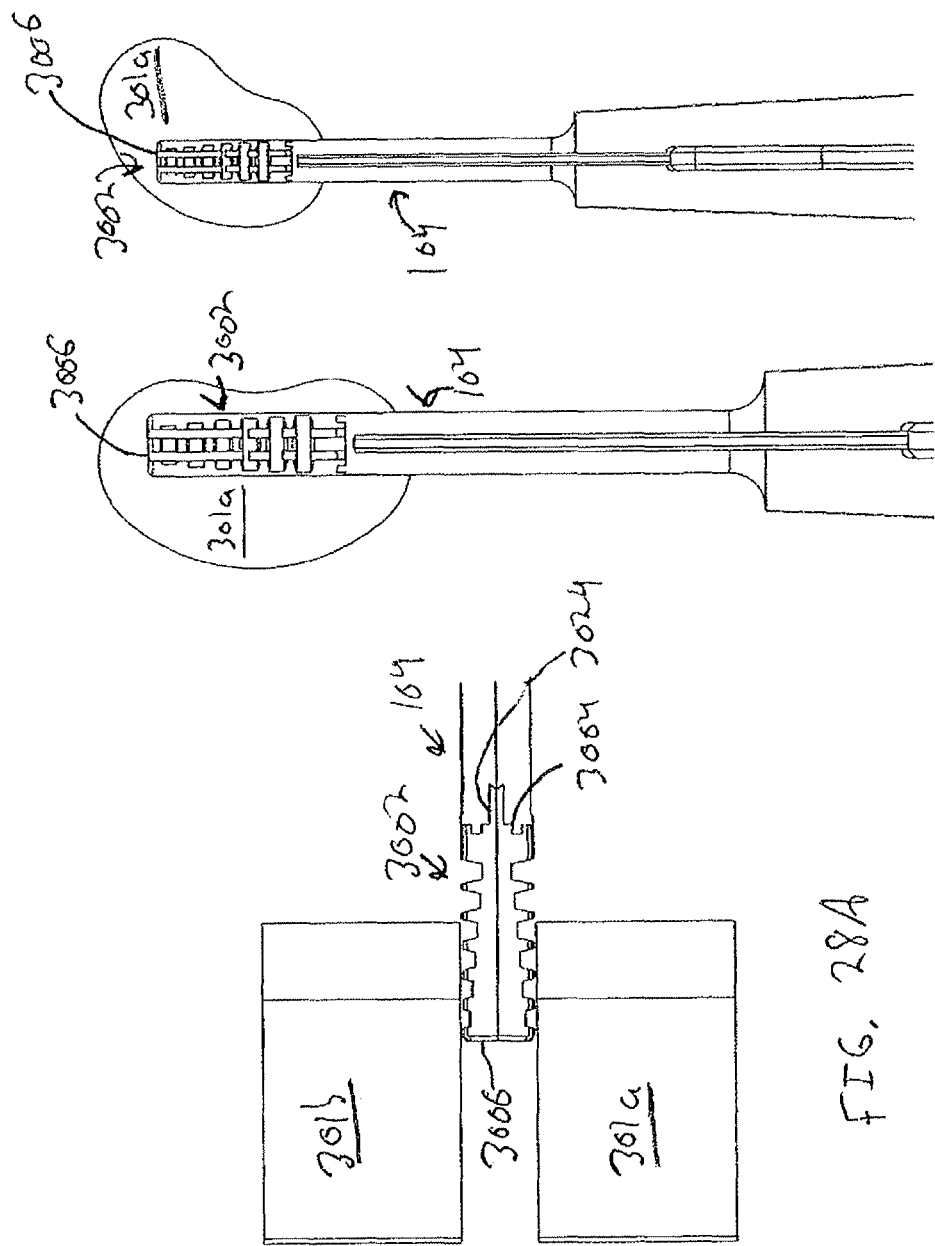

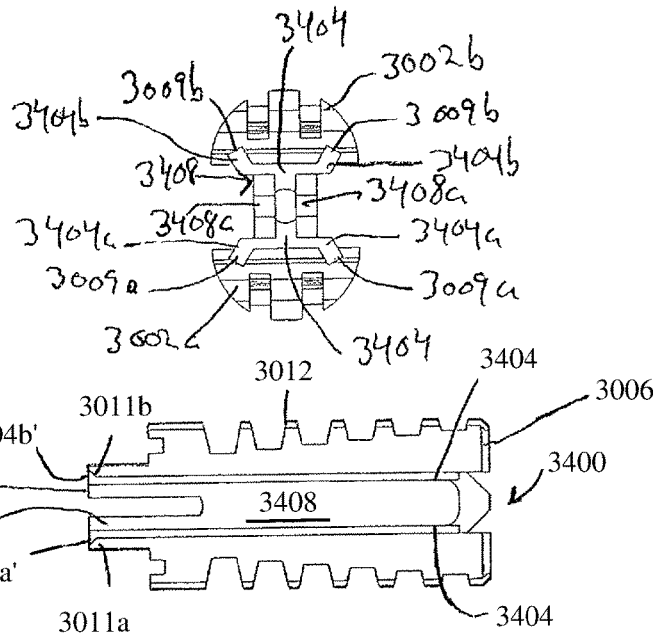
FIG. 33A
FIG. 33B
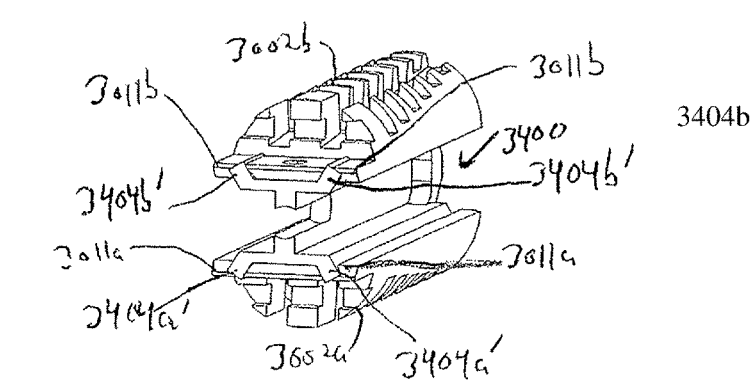
FIG. 33C
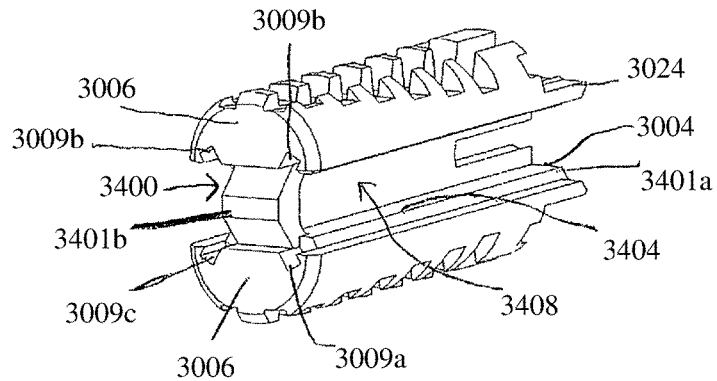
FIG. 33D

SURGICAL IMPALING MEMBER

CROSS REFERENCES TO RELATED APPLICATIONS

This application claims priority from and is related to U.S. Provisional Patent Application Ser. No. 61/652,247, entitled: Split Screw, filed on May 28, 2012, and Ser. No. 61/671,812, entitled: Split Screw with Lateral Impaling, filed on Jul. 16, 2012, the disclosures of both of the aforementioned provisional patent applications are incorporated by reference herein.

TECHNICAL FIELD

The present invention is directed to mechanical implants for spinal and other orthopedic surgeries.

BACKGROUND

Back and spinal disc surgery remains a difficult and tedious process. Accessing spinal discs is extremely complicated, as soft tissue is traumatized and sacrificed, with the length of convalescence proportional to the amount of the surgical impact on the soft tissue. Moreover, conventional spinal disc surgery causes traction on organs and tissues in the path of the surgical instrumentation needed to access the annulus.

Accessing the annulus may require passage through the ilio-psoas muscle, which houses the lumbar plexus. When instrumentation is passed through these muscles to access the annulus, it is mandatory to monitor the presence of neural elements in the trajectory of the instrumentation.

In addition, almost all of the conventional surgical techniques for spinal disc surgery use retractors. The retractors are placed within a slit in the ilio-psoas muscle, and the retractor blades are commonly fixed by screws or pins driven into the vertebral bodies, which border the disc being accessed. The blades must be pushed apart with the utmost of care, to avoid plexus injuries, which if they occur, could cause serious, or even fatal, injury to the patient.

SUMMARY

The present invention improves on the conventional art, as it provides devices and methods for avoiding neurologic iatrogenic damage of the lumbar plexus elements such as apraxia. Additionally, use of the present invention is minimally invasive, as it requires one pass close to the neural elements in accessing the annulus. The present invention also provides methods and apparatus which deploy impaling members, such as screws, between vertebral bodies, and then separate (move apart) the impaling member into portions which impale the tissue, e.g., bone, such as the compact or cortical bone of the vertebral bodies, and attach thereto. With the portions of the impaling members spaced apart and attached to the bone, implants and other instrumentation may be secured to the portions of the impaling member.

The present invention provides implants for orthopedic surgery, which include an impaling member, which is separable into portions for impaling and attaching to tissue, for example, bone. Once the portions of the impaling member are separated and attached to the requisite tissue, they may accommodate stabilizing members for fixation, or other instrumentation for procedures such as fusion.

An embodiment of the invention is directed to an apparatus for deploying an implant. The apparatus comprises a dilator or dilator member which operates in a cooperative manner with a tissue impaling member. The dilator member comprises a plurality of portions, each portion of the plurality of portions separable from each other and movable between a closed position and open positions. The tissue impaling member comprises a plurality of portions separable from each other, and is removably attachable to a corresponding portion of the dilator member, each of the portions of the tissue impaling member when attached to the corresponding dilator member portion, are movable between the closed position and open positions in accordance with the movement of the portions of the dilator member between the closed position and open positions.

Another embodiment of the invention is directed to a method for deploying an impaling member in tissue, for example, bone. The method comprises providing an apparatus for deploying an implant, comprising: a dilator member comprising a plurality of portions, each portion of the plurality of portions separable from each other and movable between a closed position and open positions; and; a tissue impaling member comprising a plurality of portions separable from each other and removably attachable to a corresponding portion of the dilator member, each of the portions of the tissue impaling member when attached to the corresponding dilator member portion, movable between the closed position and open positions in accordance with the movement of the portions of the dilator member between the closed position and open positions. A surgical site is accessed with the apparatus. The dilator member is moved (distracted) so as to separate the dilator member into portions, and correspondingly move the tissue impaling member, so as to separate the tissue impaling member into portions. The forces of the separation are sufficient to cause the impaling member to impale the tissue at the surgical site and attach the portions of the tissue at the surgical site.

BRIEF DESCRIPTION OF THE DRAWINGS

Attention is now directed to the drawings where like numerals or characters represent like or corresponding components. In the drawings:

FIG. 1D is a side view of the impaling member and dilator member of the apparatus of FIG. 1A;

FIG. 2 is a side view of an impaling member of the apparatus of FIG. 1A, with its portions spaced apart from each other of the;

FIG. 10A is a perspective view of a separator member used with the apparatus of FIG. 1A;

FIG. 10B is cross sectional view of the separator member of FIG. 10A taken along line 10B-10B of FIG. 10A;

FIGS. 13 and 14 are side views showing an exemplary operation of the apparatus of FIG. 1A with separator members therein;

FIG. 15 is a side view of a screw of the apparatus deployed in the body;

FIGS. 16A and 16B are perspective views of the deployment of a C-Beam in accordance with an embodiment of the invention;

FIG. 27D is a perspective view of the alternative impaling member of FIG. 26 split into portions;

FIGS. 28A and 28B, are diagrams detailing deployment of the alternative impaling member of FIG. 26;

FIGS. 28C-1 and 28C-2, are diagrams detailing deployment of the alternative impaling member of FIG. 26 at various locations with respect to the vertebral bodies;

FIGS. 33A and 33B are cross sectional views of the I-Beams attached to the impaling member of FIG. 26;

FIG. 33C is a rear (proximal) view of the I-Beam attached to the impaling member of FIG. 26; and FIG. 33D is a front (distal) view of the I-Beam attached to the impaling member of FIG. 26.

DETAILED DESCRIPTION

Figure 3:
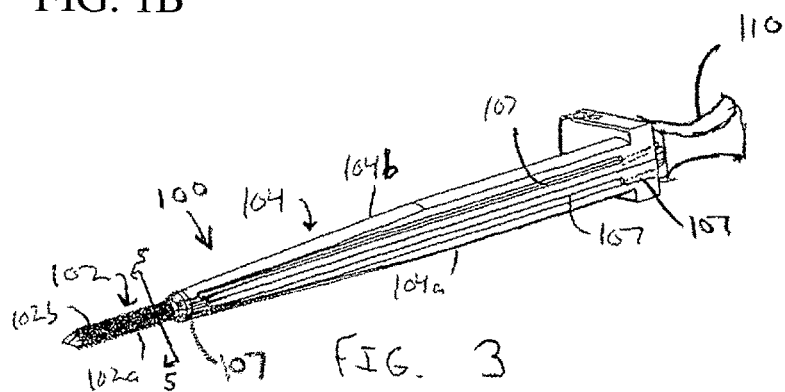
FIG. 3 is a cross-sectional view of the apparatus of FIG. 1C taken along line 3-3 of FIG. 1C.
Figure 1A:
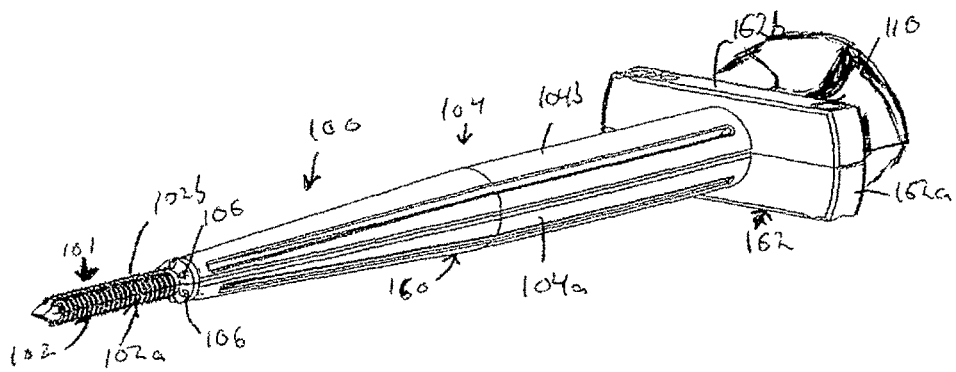
FIG. 1A is a perspective view of the apparatus in accordance with an embodiment of the invention.
Figure 1C:
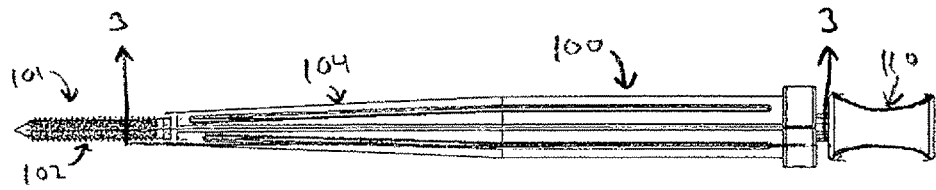
FIG. 1C is a side view of the apparatus of FIG. 1A.

FIGS. 1A to 1D show an apparatus 100 in accordance with the present invention. The apparatus 100 includes an impaling member 101, for example, a screw 102, for impaling and attaching to, for example, body tissues, such as bone. The screw 102 is removably joined to a dilator 104 (also known as a dilator member). The screw 102 and the dilator 104 are both formed of plural portions, 1022a, 102h of the screw 102, and 104a, 104b of the dilator 104, the plural portions, for example, are halves. The respective portions of the screw 102 and dilator 104 (i.e., 102a and 104a, and 102b and 104b) are separable with respect to each other, for example, as they are designed to be spaced apart (by being moved apart) from each other laterally or in a vertical direction (depending on the orientation) (represented by the double headed arrow 112), between a closed position as shown, and various open or spaced apart positions at separation distances (ds), represented as shown in FIG. 2, and detailed below. The screw 102 is removably connected to the dilator 104 by removable rods 106, which extend through bores 107 of the dilator portions 104a, 104b, as shown in FIG. 3.

Figure 4A:
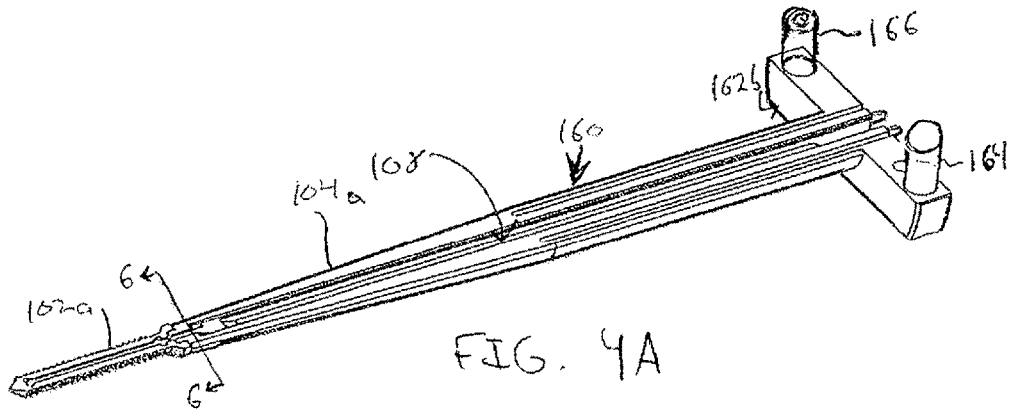
FIG. 4A is a perspective view of a distal portion of the apparatus of FIG. 1A.
Figure 4B:
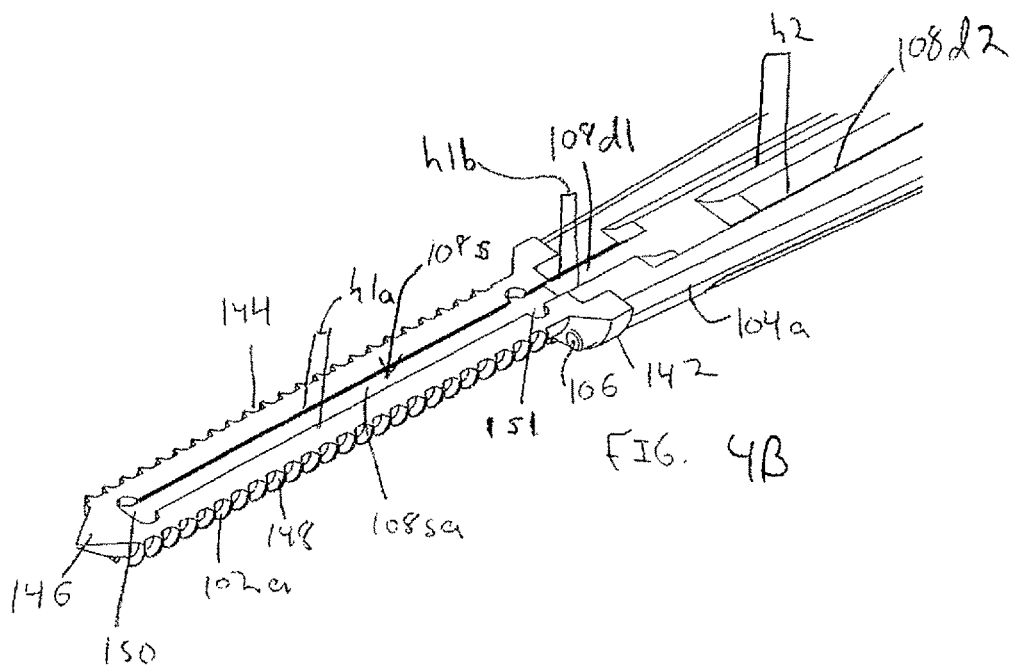
FIG. 4B is a detailed perspective view of a portion of the apparatus of FIG. 1A.

Turning also to FIGS. 4A and 4B, a common track 108 extends through the dilator 104 and the screw 102. The track 108 includes a portion 108s in the screw 108, and portions 108d1 and 108d2 in the dilator 104.

Figure 5:
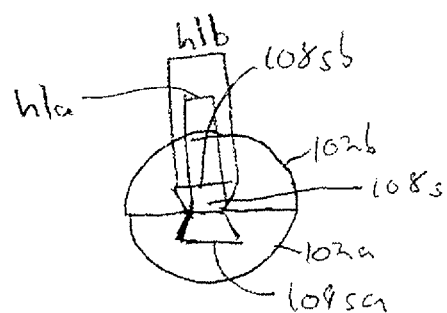
FIG. 5 is a cross sectional view of the apparatus of FIG. 1A taken along line 5-5 of FIG. 3.
Figure 6:
FIG. 6 is a cross sectional view of the apparatus of FIG. 1A taken along line 6-6 of FIG. 4A.

The portion of the track 108s in the screw 102 is dual dovetailed, formed of dovetailed portions 108sa and 108sb of horizontal dimensions (h1a) and (h1b), as shown in FIGS. 4B, 5 and 6. The track portions 108d1 and 108d2 in the dilator 104, as shown in dilator portion 104a, and are of constant horizontal dimensions for the small track portion 108d1 (h1b) and for the large track portion 108d2 (h2) respectively. For example, dimension h2 is greater than dimension h1b, which is greater than horizontal dimension h1a. The vertical dimensions (elevations) of each track portion 108s, 108d1 and 108d2 are different.

The track 108 is designed to accommodate a screwdriver member 110 (FIGS. 9A and 9B), as well as separator members 180 (FIGS. 10A and 10B), for separating (moving apart) the screw/dilator portions 102a/104a, 102b/104b from each other, as shown in FIGS. 13 and 14, and detailed below.

Figure 17A:
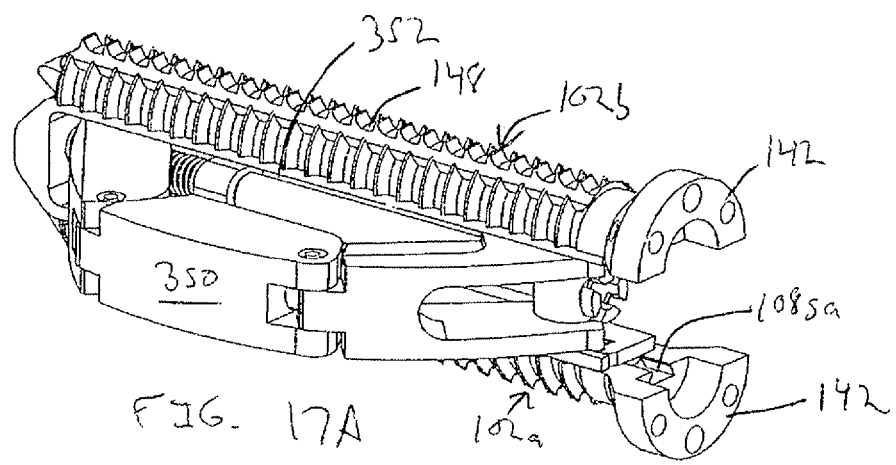
FIGS. 17A and 17B are perspective views of the C-Beams of FIGS. 16A and 16B deployed in screws having been separated in accordance with an embodiment of the invention.
Figure 17B:
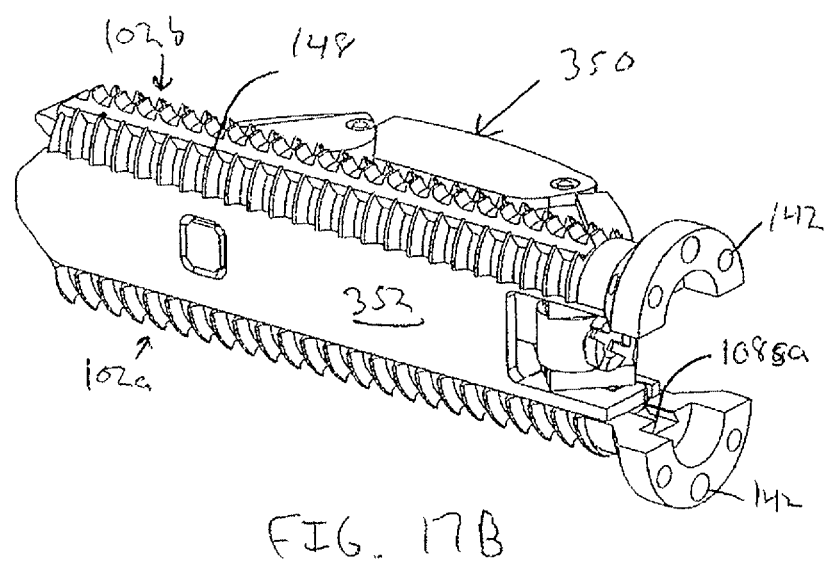
Figure 18A:
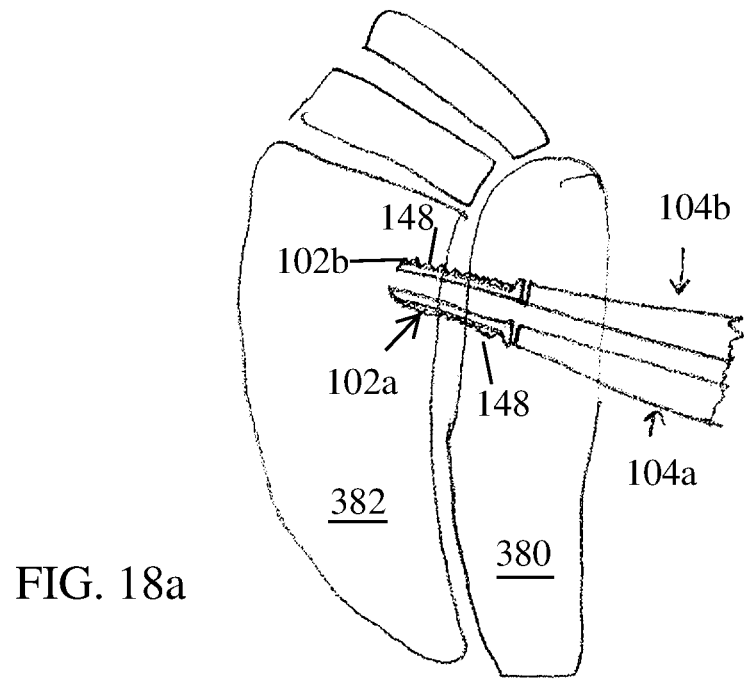
FIG. 18A is a view of the apparatus in an exemplary operation at the sacro-iliac joint.
Figure 18B:
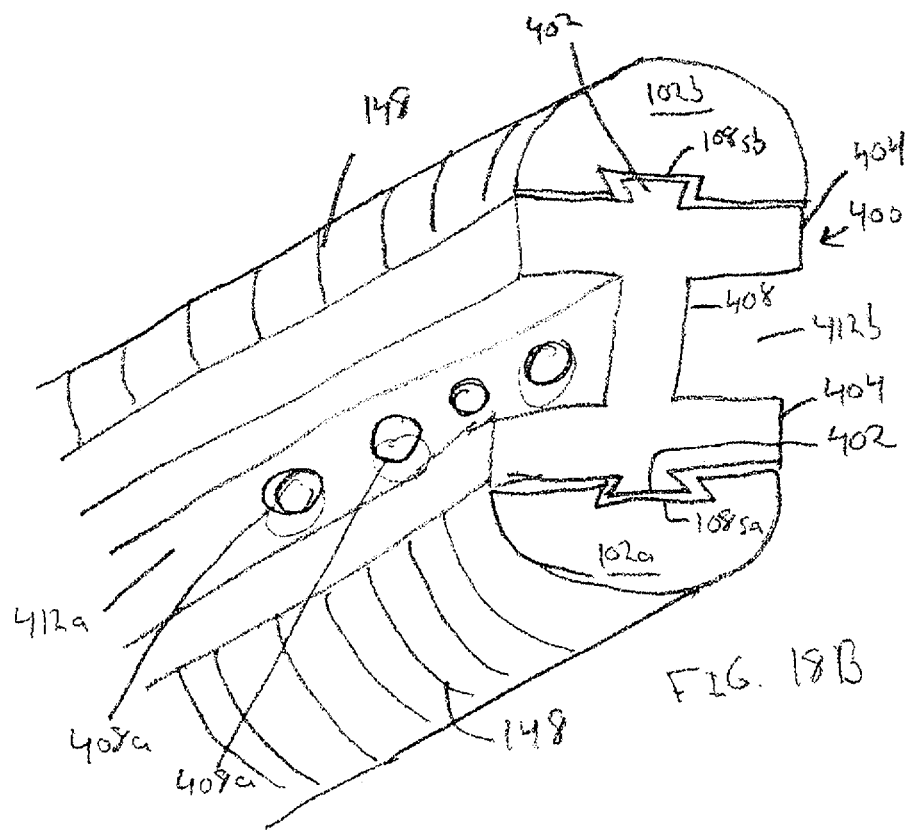
FIG. 18B is a perspective view of an I-Beam deployed in a screw having been separated in accordance with that shown in FIG. 18A.

The track 108 is designed to accommodate a screwdriver member 110, and one or more separator members 180, of increasing vertical dimensions, inserted and removed from the track 108 of the apparatus 100 in succession, to progressively increase the distance between the screw/dilator portions 102a/104a, 102b/104b from each other, as shown in FIG. 2 and detailed below. The portion of the track 108s in the screw 102 is also configured to accommodate a C-beam 352, shown in FIGS. 16A, 16B, 17A and 17B, and an I-beam 400, as shown in FIG. 18B, and both as detailed below.

The screw 102 and dilator 104, for example, are both divided axially at their midlines 102x, 104x (FIG. 1D) into two portions, e.g., halves. 102a, 102b (screw 102), 104a, 104b (dilator 104), as shown in FIG. 2. The screw portions 102a, 102b are typically symmetric with respect to each other, both externally and internally, but may be not be completely symmetric externally depending on the thread pattern, such as one which helically traverses the screw 102. The dilator portions 104a, 104b are typically symmetric with respect to each other, both externally and internally.

Figure 1B:
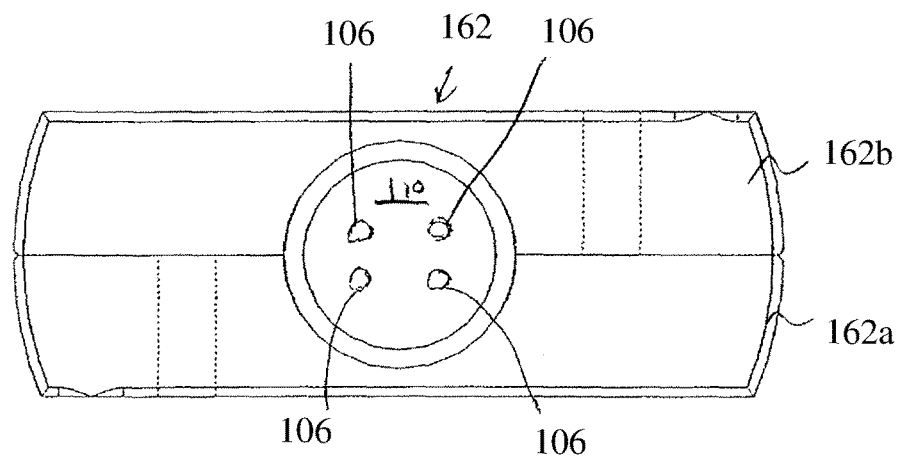
FIG. 1B is a rear view of the apparatus of FIG. 1A.
Figure 7A:
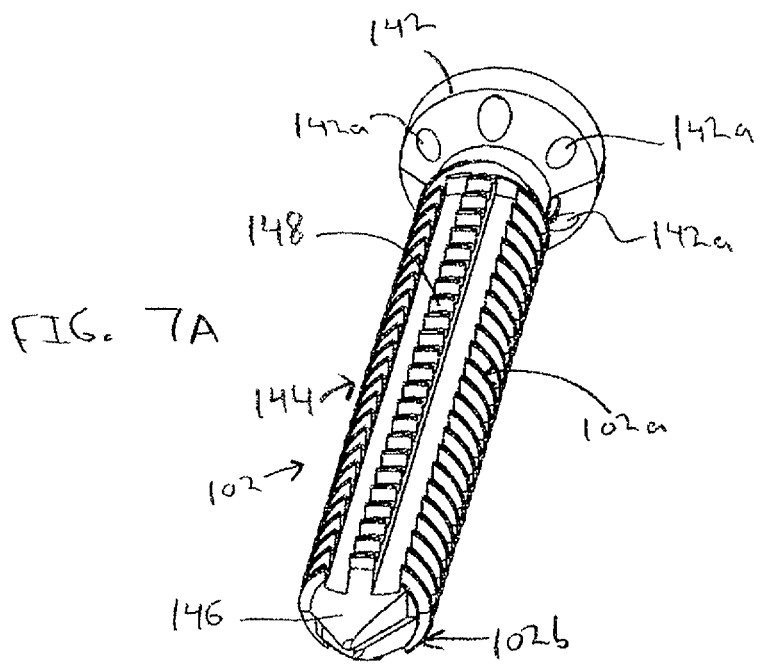
FIGS. 7A and 7B are perspective of screws used with the apparatus of FIG. 1A.
Figure 7B:
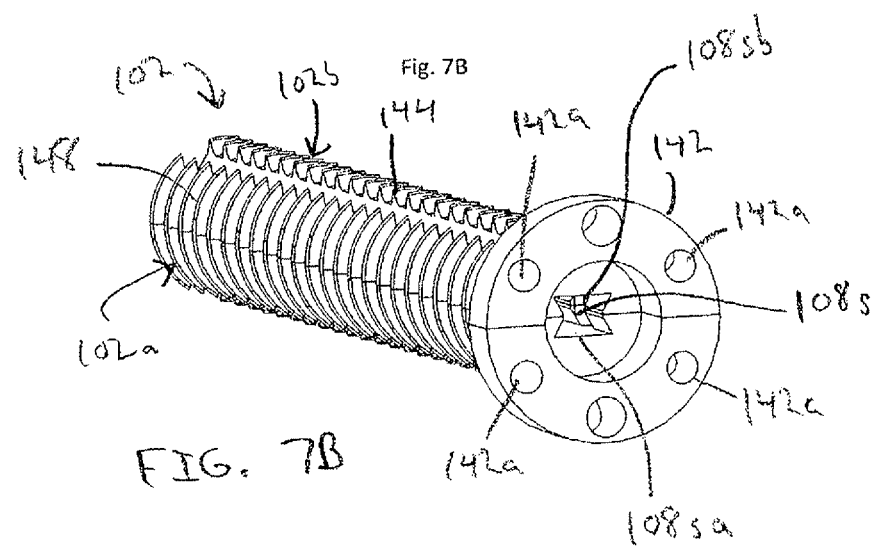

Turning to FIGS. 7A and 7B, where the screw 102 is in the closed position, and FIG. 2, where the screw 102 is in the open position, the screw 102 includes a head 142 (defining the proximal end of the screw 102), shank 144, and a tip 146 (defining the distal end of the screw 102). The head 142 includes openings 142a, which are internally threaded, that receive the rods 106, with corresponding threading, which attach and hold the screw 102 on the dilator 104. As shown in FIGS. 1B and 4A, the rods 106 extend through the dilator 104, and protrude beyond the dilator 104, so that the rods 106 can be removed, when it is desired to disengage the screw 102, i.e., disengage the screw portions 102a, 102 from the respective dilator portions 104a, 104b, once the screw portions 102a, 102b) are successfully attached to (by impaling) each of the respective vertebrae, as shown, for example, in FIGS. 12 and 15, and detailed below. The screw 102 is made of, for example, materials including surgical grade steel, polymers and the like.

The shank 144 of the screw 102 extends from the head 142 to the tip 146, and is threaded by threads 148. The threads 148 are arranged any one of numerous patterns and, pitches. For example, the threading may be discontinuous, or furrowed, as shown, or continuous. The threads 148 are designed to be sharp, to easily impale the cortical or compact bone of the vertebrae or other tissue.

The tip 146 at the distal end of the screw 102 is, for example, pointed, or angled inward. This allows for the screw to be deployed between vertebrae by screwing (twisting) the apparatus 100, or the surgeon tapping the screw 102 into position.

The dilator 104, when engaged with the screw 102, allows the screw 102 to be moved from a closed position, where the portions 102a, 102b of the screw 102 are joined together, to an open position, where the portions 102a, 102b of the screw 102 are spread apart or separated from each other, as shown for example in FIG. 2. The dilator portions 104a, 104b simultaneously move from the aforementioned closed position to the aforementioned open position, corresponding to those positions of the screw 102.

Turning back to the portion of the screw 102a, in FIGS. 4A and 4B, which, as shown, is symmetric with the other portion 102b (not shown), in all aspects, externally and internally, and accordingly, is representative of the other portion 102b of the screw 102. The track portion 108sa in this screw portion 102a combines with the corresponding track portion 108sb in the screw portion 102b to form the track portion 108s in the screw 102. Each track portion 108sa, 108sb includes cut outs 150, 151 at its ends and each track portion 108sa, 108sb is dove tailed, as shown in FIG. 5. The cut outs 150, 151 are of a width greater than the horizontal dimension (h1), to serve as tactile stops/locking sites for a C-Beam 352, shown in FIGS. 16A-16D and detailed below, and an I-beam 400, as shown in FIG. 18B and detailed below. The dove tail shape of the track portions 108sa, 108sb serves to securely receive, allow for movement of, and retain the aforementioned C-Beams 352 and I-beams 400, by the screw portions 102a, 102b, as detailed below.

The dilator 104 is formed of a conical segment 160 which extends from a plate 162. Like the screw 102, each of the symmetric portions 104a, 104b of the dilator 104, cooperatively form the portion 108d of the track 108 in the dilator 104 (conical segment 160 and plate 162).

Figure 8:
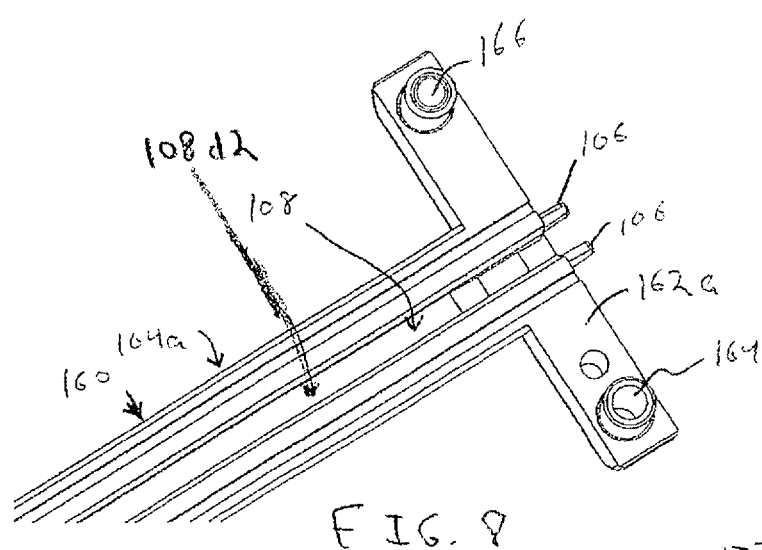
FIG. 8 is a perspective view of a proximal portion of the apparatus of FIG. 1A.

As shown in FIG. 8, as represented by a dilator portion 104a, each portion 162a, 162b of the plate 162 includes a bore 164 and a corresponding pin 166. Each pin 166 is received in the respective bore 164. The pins 166 within each corresponding bore 164 are in a male-female engagement, which is frictionally snug.

This frictionally snug male-female engagement allows for movable separation (moving apart) of the dilator portions 104a, 104b. The tolerances between each pin 166/bore 164 engagement are sufficiently tight, such that the pins 166 move vertically in the respective bores 164 only after substantial force is applied to the dilator portions 104a, 104b, by movement of separator members 180 (FIGS. 13 and 14) upon their entry into the track 108 of the apparatus 100, as detailed below. The aforementioned tolerances are also such that the pins 166 are inhibited from sliding laterally in the bores 164. As a result of the aforementioned tolerances, the screw portions 102a, 102b and dilator portions 104a, 104b, when moved apart from each other (e.g., when the dilator portions 104a, 104b are moved apart from each other, resulting in the attached screw portions 102a, 102b also moving apart), are maintained at equal or approximately equal separation distances (ds), as shown in FIG. 2, and as further detailed below. The dilator 104 is made of, for example, materials including surgical grade steel, polymers and the like.

Figure 9B:
FIG. 9B is cross sectional view of the screwdriver member of FIG. 9A taken along line 9B-9B of FIG. 9A.
Figure 9A:
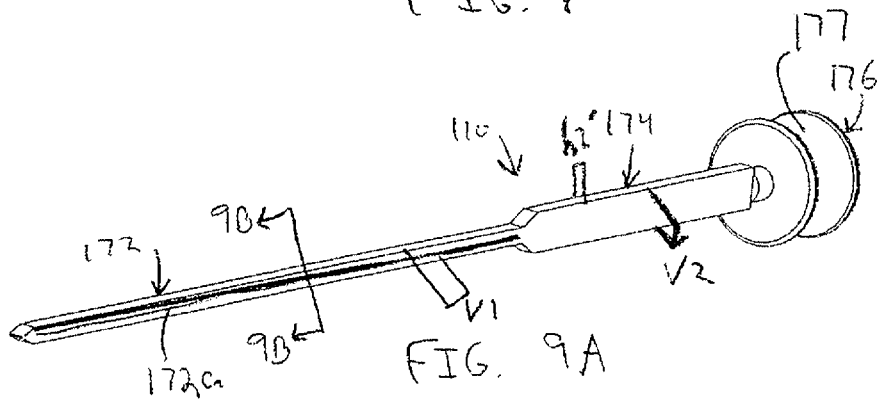
FIG. 9A is a perspective view of a screwdriver member used with the apparatus of FIG. 1A.

FIGS. 9A and 9B show the screwdriver member 110, which slideably fits in the track 108 when the screw 102 and dilator 104 are in the closed position. The screwdriver member 110 is in the track 108 of the apparatus 100 when the screw 102 is being deployed in the body, for example, between vertebrae. The screwdriver member 110 has horizontal dimensions, which are slightly less than the corresponding horizontal dimensions of the track 108 (such as dimension h2' of the proximal portion 174, which is slightly less than horizontal dimension h2 of the corresponding track portions 108d2 of the dilator portions 104a, 104b). The vertical dimensions of the portions-distal 172 ($v1$), and proximal 174 ($v2$), of the screwdriver member 110 are less than the vertical dimensions of the corresponding portions 108s, 108d of the track 108, whereby the apparatus 100 remains in the closed position, when the screwdriver member 110 is in the track 108 of the apparatus 100.

The screwdriver member 110 includes a distal portion 172, for fitting in the track portion 108s, 108d1 of the screw 102, and the dilator 104, respectively, and a proximal portion 174, for fitting in the track portion 108d2 of the dilator 104. The distal portion 172 is shaped to correspond to the dovetail shape of the track portions 108sa, 108sb (FIG. 5) in the screw 102, as shown by the cross section of FIG. 9B. The dovetailed outer surfaces 172a of the distal portion 172 fit within the dovetailed track portions 108sa, 108sb, to hold the screw portions 102a, 102b together, in place, in the closed position, during entry of the apparatus 100 into the body and deployment of the impaling member 101, e.g., the screw 102, between the vertebrae, as detailed below.

The proximal portion 174 terminates in a head 176, which, for example, is grooved (with the groove 177), to be graspable by the surgeon for insertion and removal of the screwdriver member 110 with respect to the track 108 of the apparatus 100. The screwdriver member 110 is such that it is, for example, manually pushed into the track 108 of the apparatus 100 when inserting the screwdriver member 110 into the apparatus 100, and, for example, manually pulled out of the track 108 of the apparatus 100. This manual movement is possible as the screwdriver member 110 is not under load when in the track 108 of the apparatus 100.

However, the screwdriver member 110 may be tapped into the track 108 of the apparatus. 100 by the surgeon with a surgical hammer or the like, if desired.

The screwdriver member 110 is, for example, made of materials such as surgical stainless steel or other surgical grade metals and polymers, as well as other biocompatible materials. The screwdriver member 110, as shown is two pieces, for example, the head 176 as one piece and the proximal 174 and distal 172 portions as the other piece. Other single piece or multiple piece combinations for the screwdriver member are also permissible.

FIGS. 10A and 10B show a separator member 180, representative of the separator members used with the apparatus 100. The separator member 180, includes a distal portion 182, including protrusions 182a (shown as rectangular but may be rounded) extending along the distal portion 182, for fitting into the track portions 108sa, 108sb of the screw 102. A proximal portion 184 is for fitting in the track portion 108d of the dilator 104. The proximal portion 184 terminates in a head 186, which includes a bore 188 (oriented substantially perpendicular to the outwardly extending proximal portion 184), for receiving a stub 210a of a handle 200, for moving the separator member 180 into and out of the track 108 of the apparatus 100 as shown in FIGS. 13 and 14 and detailed below.

The separator member 180 is, for example, made of materials such as medical grade polymers, in order to minimize friction when the separator member 180 slides into and out of the track 108 of the apparatus 100. The separator member 180 as shown is a single integral piece. However, the separator member 180 may be made of multiple pieces.

Each separator member 180, for example, has a constant horizontal dimension (h2'), which is slightly less than the horizontal dimension (h2) of the track portion 108d2 of the dilator 104. The vertical dimensions (v) of each separator member 180 (the portions 182 (v3), 184 (v4) thereof) are different, allowing for progressively increased spacing between the screw 102a, 102b and dilator 104a, 104b portions, when these portions are spread apart by the separator members 180, with increasing vertical dimensions, by the separator member 180 being placed into the track 108 of the apparatus 100. The forces created by the separator member(s) 180 upon their completion of movement into the track 108, to move the dilator portions 104a, 104b apart from each other, provides impaling forces for the screw threads 148 of the screw portions 102a, 102b to impale the cortical or compact bone of the respective vertebrae (vertebral bodies). This impaling results in a strong engagement and attachment of the respective screw portion 102a, 102b into the vertebrae 301a, 301b, as shown, for example, in FIG. 15.

The separator member 180 slideably fits in the track 108 when the screw 102 and dilator 104 are in the closed position, as shown in FIG. 1, and on completion of its insertion into the track (the insertion is performed, for example, by tapping the head 186 of the separator member 180 into the track 108 of the apparatus 100), have moved the screw portions 102a, 102b and dilator portions 104a, 104b apart by a separation distance (ds) (FIG. 2). The separator member 180 is in the track 108 of the apparatus 100 when the screw 102 is at the deployment site (e.g., between vertebrae), and is its portions 102a, 102b, between and in some cases, embedded in the respective vertebrae, are to be spread apart.

There are, for example, multiple separator members 180 for use with the apparatus 100. Each separator member 180, for example, is of the same or approximately the same horizontal dimension (h2'), but at variable vertical distances, to be employed sequentially, to sequentially (progressively) space the screw 102a, 102b and corresponding dilator 104a, 104b portions at various spaced apart distances (ds, as shown in FIG. 2). Separator members 180 are typically employed in succession based on the vertical dimension, the smallest vertical dimension being used first, with larger vertical dimensioned (v) separators 180 being slid into the apparatus 100 in succession (after the previous separator member 180 has been removed from the track 108 of the apparatus 100).

For example, successive separator members 180, increasing in vertical dimensions, are employed, such that spacing apart of the screw 102a, 102b and corresponding dilator 104a, 104b portions is progressive, until the surgeon arrives at the desired spaced apart distance for screw 102 deployment. Each separator member 180, upon its being placed into the track 108 of the apparatus forces the screw 102a, 102b and dilator 104a, 104b to spread apart, at an increased distance from the previous separator member 180. The force created by the separator member 180 in spreading apart the screw 102a, 102b and dilator 104a, 104b portions, creates forces which impale the screw portions 102a, 102b, via the threads 148, in the cortical or compact bone of the respective vertebrae, as detailed below.

Figure 11A:
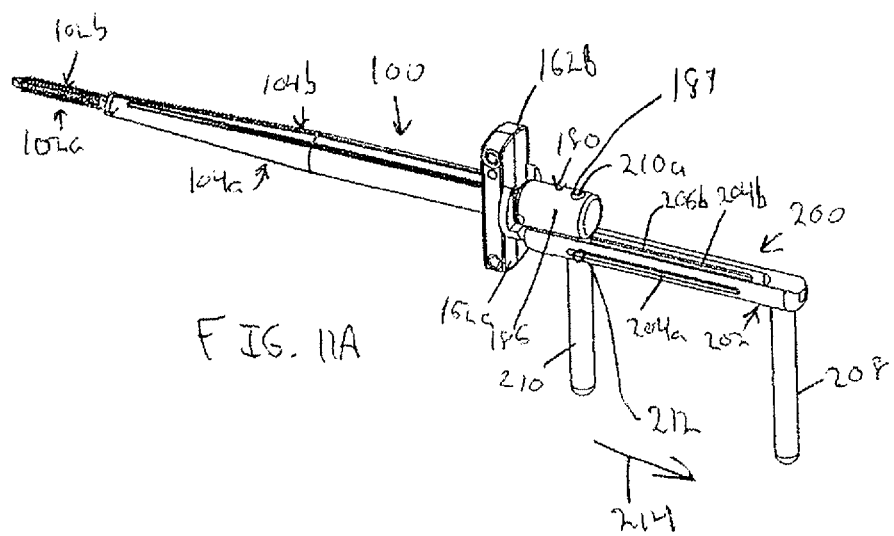
FIGS. 11A and 11B are perspective views of the apparatus of FIG. 1A in operation with a handle.
Figure 11B:
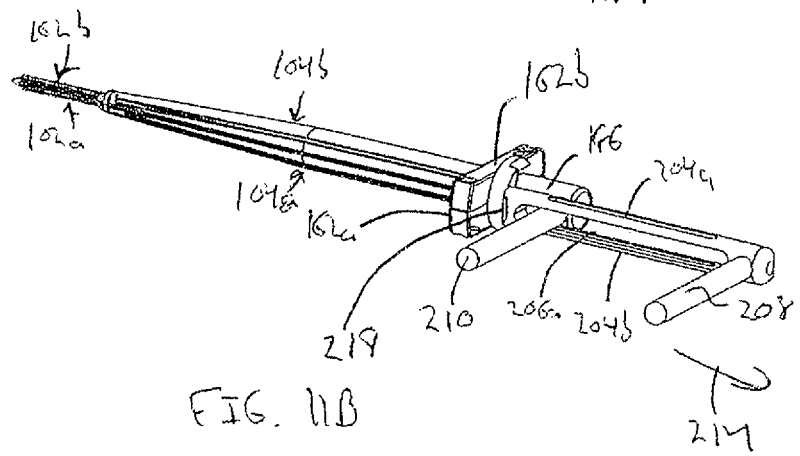

The separator member 180 typically works with a handle 200, as shown in FIGS. 11A and 11B, on its removal from the apparatus 100. The screwdriver member 110 may also be designed with a bore in its head 176, to receive the handle, as detailed below. Should the screwdriver member 110 be used with the handle 200, use would be in accordance with that detailed for the separator member(s) 180 below.

The handle 200 includes a body 202, having first aligned slots 204a, 204b, and second aligned slots 206a, 206b. An anchor rod 208 is fixedly attached to the body 202 at its proximal end, and a moveable rod 210, includes a stub 210a for fitting into the bore 188 of the head 186 of the separator member 180. The movable rod 210 includes lateral pins 212 to ride in the first aligned slots 204a, 204b, while the rod 210 moves within the confines of the second aligned slots 206a, 206b, for example, in the direction of the arrow 214.

In an example operation of the handle 200, the nose 218 at the distal end of the body 202 abuts the plate 162 or plate portion 162a, 162b (if the apparatus 100 is in an open position) in the dilator 104. The movable rod 210 is pulled toward the anchor rod 208 (in the direction of the arrow 214) with both rods 208, 210 typically being gripped by the surgeon. The lengths of the first 204a, 204b and second 206a, 206b aligned slots are slightly greater than the track portion 108s in the screw 102, as compression forces on the screwdriver member 110 and separator member 180 are greatest in this track portion 108s, typically requiring assistance of the handle 200 for removal of the separator member 180 from at least this portion 108s the track 108. Once moved to the proximal most position by the moveable rod 210, the separator member 180 can be finally removed from the track 108 of the apparatus 100 by being manually pulled out of the apparatus 100.

Figure 12:
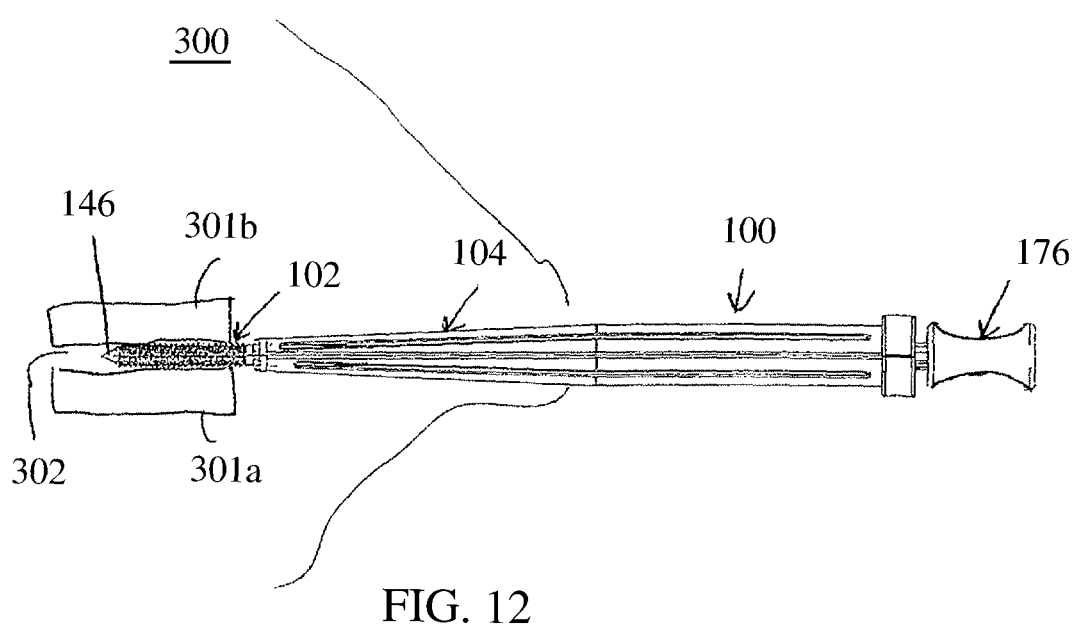
FIG. 12 is a side view showing the apparatus of FIG. 1A in an exemplary operation.

FIGS. 12, 13, 14 and 15 detail an exemplary operation of the apparatus 100. Initially, as shown in FIG. 12 the apparatus 100 enters the side of the body 300, and the screw 102 is between vertebrae 301a, 301b, in the disc space 302. The surgeon then turns or twists the apparatus 100, to create a screw motion for the screw 102. Alternately, the apparatus 100 can be tapped with a surgical hammer or the like to position the screw 102 between the vertebrae 301a, 301b.

With the screw 102 fixed or otherwise positioned between vertebrae 301a, 301b, the screwdriver member 110 is manually removed from the track 108 of the apparatus 100, by being pulled out of the apparatus 100 by the surgeon. Separator members 180, one or more, are sequentially inserted into the track 108 of the apparatus 100, as shown in FIG. 13, by tapping on the head 186, until the separator member 180 reaches an end point, proximate to the screw tip 146, as shown in FIG. 14. The separator member 180 is removed from the apparatus 100 via the handle 200 and manually pulling the remainder out of the apparatus 100 as detailed above. This use of one or more separator members 180 continues until the desired spacing between the screw portions 102a, 102b has been achieved, as shown in FIG. 15. The separation forces created by the separator members 180 create forces (impaling forces), such that the screw threads 148 impale the vertebrae, in the cortical or compact bone, to engage and attach the respective screw portion 102a, 102b to the respective vertebrae 301a, 301b, at the desired separation distance. With this screw fixation achieved, various additional procedures, may be performed. These additional procedures include, for example, discectomy, bone grafting, spinal implants, and the like.

With all procedures complete, the rods 106 may now be removed from the screw head 142, by being twisted. This twisting unscrews the threaded connections at the screw holes 142a. The rods 106 are then pulled proximally, toward the plate 162. The dilator portions 104a, 104b are now removed from the body, leaving the screw portions 102a, 102b attached to the respective vertebrae, at the desired separation (spaced apart) distance. For example, these spaced apart positions are maintained by the C-beam 352 and I-Beam 400 remaining attached to the screw portions 102a, 102b.

One exemplary additional procedure in which the apparatus 100 is employed is deployment of a spinal implant and bone grafting, as shown in FIGS. 16A, 16B, 17A and 17B. The spinal implant 350, is, for example, an expandable implant, such as that disclosed in commonly owned U.S. Patent Application Publication No. US 2013/0041471 A1, entitled: Laterally Deflectable Implant, the disclosure of which is incorporated by reference herein. The spinal implant 350 is loaded onto a C-shaped beam 352, or C-Beam, and pushed by a pole member 354, along the dilator portions 104a, 104b and screw portions 102a, 102b, as shown in FIGS. 16A and 16B.

The C-Beam 352 includes oppositely disposed protrusions 356, extending along substantially all of the entire length of the C-beam 352, with a shape corresponding to the dovetail shape of the track portion 108sa, 108sb of each screw portion 102a, 102b. These protrusions 356 slide in the track portions 108sa, 108sb until the locking portion 150 is reached, as shown in FIGS. 17A and 17B. A tactile indication that this locking portion has been reached, stops distal movement of the C-Beam 352, and the implant 350 is extended out of the C-beam 352 for deployment in the disk space (between the vertebrae). With the implant deployed in the disk space, bone fill material (also known as fusion promoting material (PPM)) may be placed into the implant 350, which has been placed onto a vertebrae. This bone fill delivery procedure is, for example, in accordance with that disclosed in commonly owned U.S. Patent Application Publication No. US 2013/0041471 A1, entitled: Laterally Deflectable Implant. The apparatus 100 is also used in surgery on the Sacro-Iliac joint, as shown in FIGS. 18A and 18B. Use of the apparatus 100, and in particular, the screw 102 allows for simultaneous fixation of the ilium 380 and sacrum 382 bones, to fuse the joint between them. This fusion eliminates pain in this joint, as it is no longer mobile.

In the procedure, the apparatus 100 accesses the sacrum bone 380, with the screw 102, in the closed poison of FIG. 1, twisted or tapped into position, as detailed above. The apparatus 100 is dilated to the desired separation distance between the screw 102a, 102b and dilator 104a, 104b portions, such that the screw portions 102a, 102b, in particular the threading 148 thereof, impales the bones 380, 382, such that the screw portions 102a, 102b are securely attached or fixed to the bones 380, 382, as shown in FIG. 18A.

An I-beam 400 is positioned in the screw portions 102a, 102b, as a protrusion 402 on each of the major portions 404 of the I-beam 400 engages the dove tailed track portions 108sa, 108sb of the respective screw portions 102a, 102b, similar to that of the C-beam 352, as detailed above. The protrusions 402 correspond in shape to those of the dovetails of the track portions 108sa, 108sb of the screw portions 102a, 102b. The I-beam 400 also includes apertures 408a, extending through the central portion 408 of the I-beam. The I beam 400 is advanced until reaching the locking members 150 of the track portions 108sa, 108sb.

Figure 19:
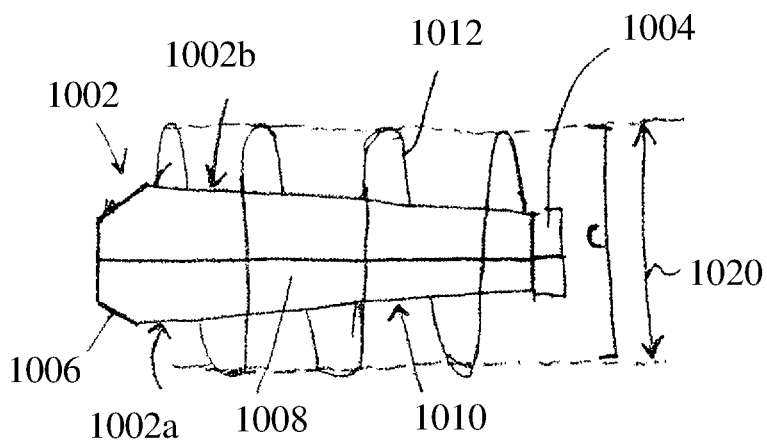
FIGS. 19 to 21 are side views of alternative screws in accordance with embodiments of the present invention.

The I beam 400 maintains the attachment of the screw portions 102a, 102b in the bone, with this attachment known as fixation. A segment of the I-beam 400 supporting the screw portions 102a, 102b in fixation is shown in FIG. 18B. If only fixation is desired, the dilator 104, in particular, the dilator portions 104a, 104b, are separated from the screw portions 102a, 102b, as detailed above, and the dilator portions 104a, 104b are removed from the body, as detailed above. If further procedures are desired, such as fusion, with the delivery of bone fill or fusion promoting material to the bones 380, 382, the material is delivered to or proximate to the I-beam 400. The material fills the areas 412a, 412b of the I-beam and typically those areas proximate thereto, by moving through the apertures 408a. Once this procedure is complete, the dilator 104, i.e., dilator portions 104a, 104b, are separated from the screw portions 102a, 102b with the I-Beam 400 remaining deployed between the remaining fixated screw portions 102a, 102b. The dilator portions 104a, 104b are removed from the body, as detailed above. FIG. 19 illustrates an alternative screw 1002, for use with the dilator 104, as detailed above. Screw 1002 includes a proximal head 1004, similar to screw head 142 and a distal tip 1006. The head 1004 is designed to attach to the dilator 104 in the same or similar manner as that of the screw 102. The shank 1008 is formed of an outward distally tapered core 1010 (taped outward toward the tip 1006). The core 1010 supports threads 1012 in numerous patterns, one such pattern illustrated in FIG. 19. The screw 1002, like the screw 102 is divided into portions 1002a, 1002b, for example, halves, which can be moved apart from each other (in the direction of the double headed arrow 1020) by separator members 180 being extended through the track 108 of the dilator 104 and screw 1002, as detailed above for the dilator 104 and screw 102.

The screw portions 1002a, 1002b are symmetric internally, and typically also externally, depending on the thread pattern. The threads 1012 are such that they are of a constant diameter (c), over the entire core 1008. Like the screw 102, the screw 1002 is of the same internal construction as the screw 102, and includes a track portion with cut outs like the track portion 108a and cut outs 150, 151 of the screw 102. As a result of this internal construction, the screw 1002, when split into its portions 1002a, 1002b, by distraction from the separator member(s) 180, as detailed above, accommodates C-Beams 352 and I Beams 400 in accordance with that disclosed above for the screw 102.

Figure 20:
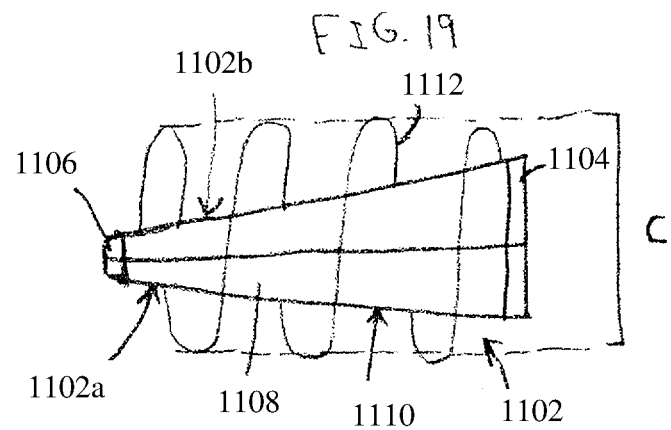

FIG. 20 illustrates an alternative screw 1102, similar to alternative screw 1002, as similar components are numbered in the "1100s." This screw 1102 differs from the screw 1002 in that the core 1110 is tapered opposite to the core 1010, and in particular is tapered outward proximately (toward the head 1104). The head 1104 temporarily attaches to the dilator 104 when in use upon screw 1102 deployment.

Figure 21:
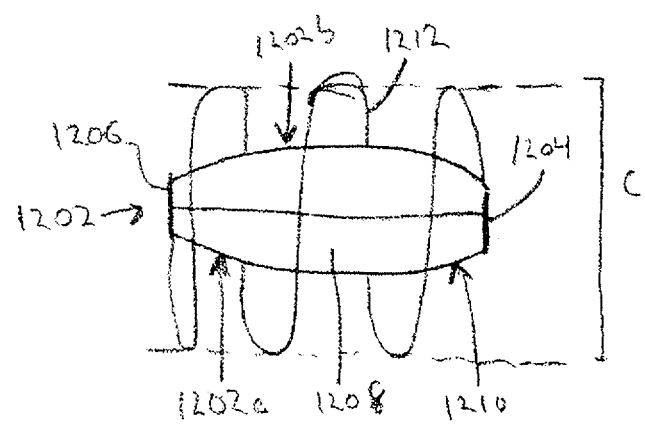

FIG. 21 illustrates an alternative screw 1202, similar to alternative screw 1002, as similar components are numbered in the "1100s." This screw 1102 differs from the screw 1002 in that the core 1210 is dual tapered inwardly at the ends, resulting in an oval-like shape. This screw 1202 is designed for implants and procedures in the domes of the vertebrae.

Figure 22A:
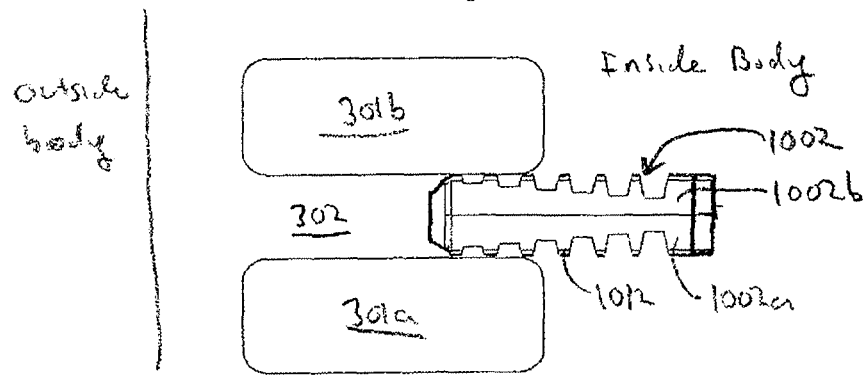
FIGS. 22A-22E are diagrams detailing an exemplary operation of the alternative screw of FIG. 19.
Figure 22B:
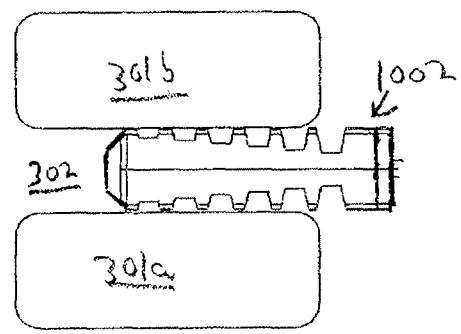
Figure 22C:
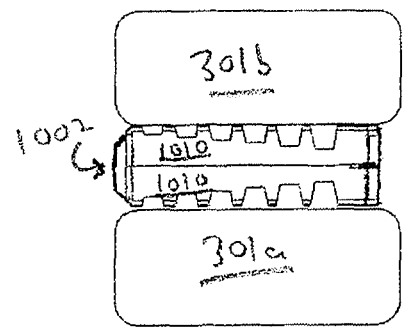
Figure 22D:
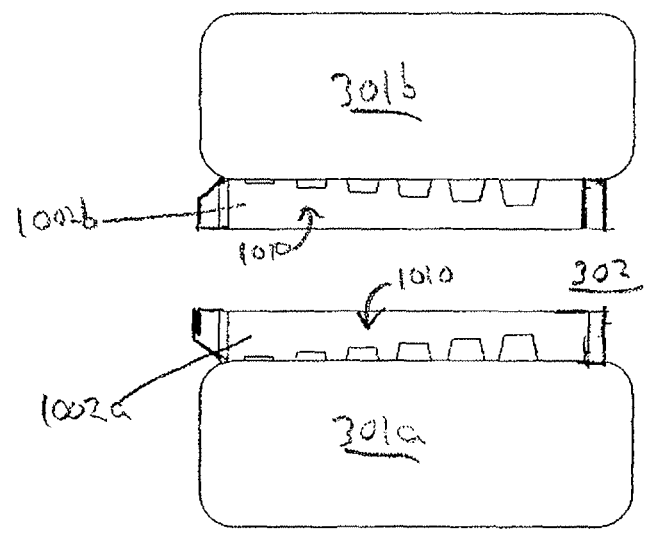
Figure 22E:
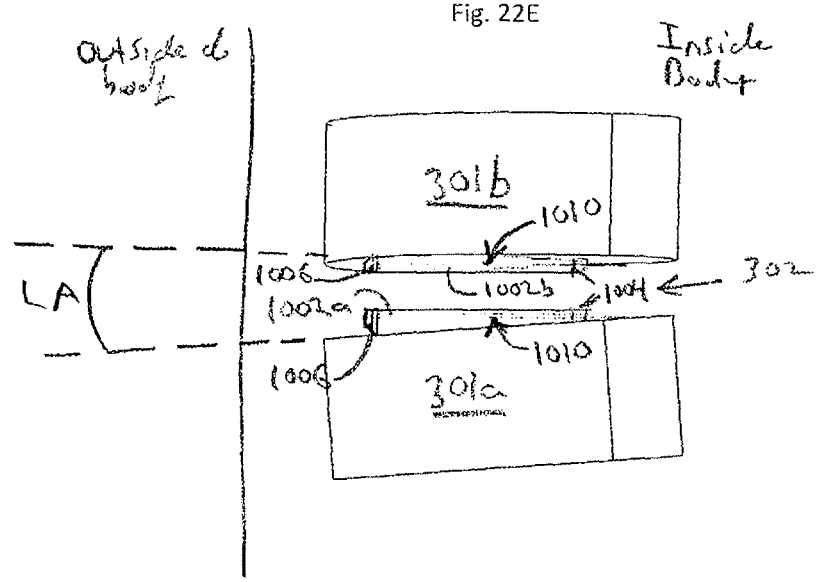

Screws 1002 and 1102 are designed to impale vertebrae 301a, 301b at angles corresponding to the tapering of the core 1010. For example, as shown progressively in FIGS. 22A to 22E, the screw 1002 once deployed, and upon screw portions 1002a, 1002b being moved apart, impales in the vertebrae 301a, 301b. Impalement extends to the core 1010, so as to cause an angle in accordance with the lordotic curvature or angle (LA of FIG. 22F) of the spine.

Screw 1102 is designed to cause angling of the vertebrae at an opposite angle to that for the screw 1002. The screw 1102, is used in treating scoliosis, as from a single point of concavity, to oppose the direction of the scoliosis curvature.

Figure 23:
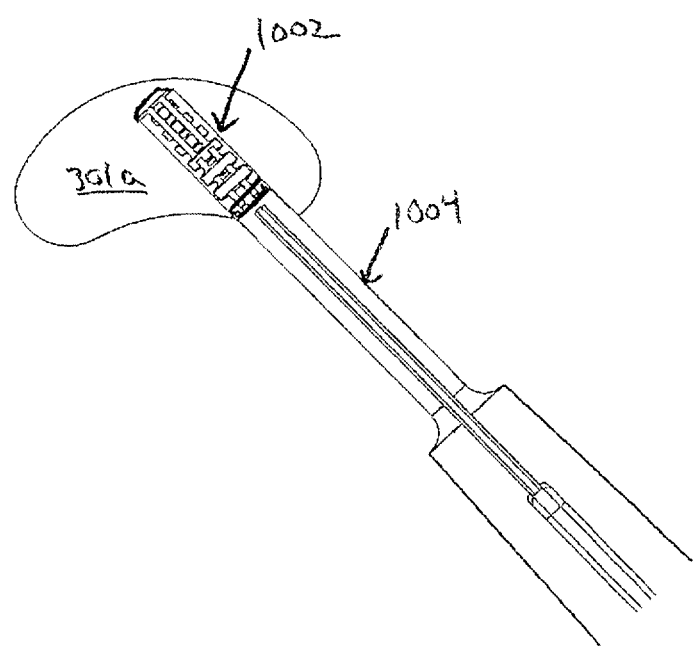
FIG. 23 is a diagram showing deployment of the alternative screw of FIG. 19.

All of the aforementioned alternative screws 1002, 1102 and 1202 are deployed by the dilator 104 in accordance with the methods disclosed above. For example, in FIG. 23, the screw 1002 is shown being deployed with the dilator 104 over a pedicle (not shown) of a disk 301a, in accordance with the procedures detailed above. Screw 1002 on the dilator 104 is representative of screws 1102 and 1202, which can be deployed on the dilator 104 in the same manner.

Additionally, the deployment is such that the screws 1002, 1102 and 1202 can be screwed into the respective disk space or tapped into the disc space, between the vertebrae. These screws 1002, 1102, 1202, when deployed by the dilator 104, as detailed above, and split into portions 1002a, 102b, 1102a, 1102b, 1202a, 1202b, impale the respective vertebrae, and engage the respective vertebrae, at angles with respect to the respective cores 1010, 1110 and 1210. The now spaced apart screw portions 1002a, 1002b, 1102a, 1102b, 1202a 1202b can accommodate C-beams and I-beams as detailed for the screw 102 above, and can be used in the procedures associated therewith, as described above.

Figure 24:
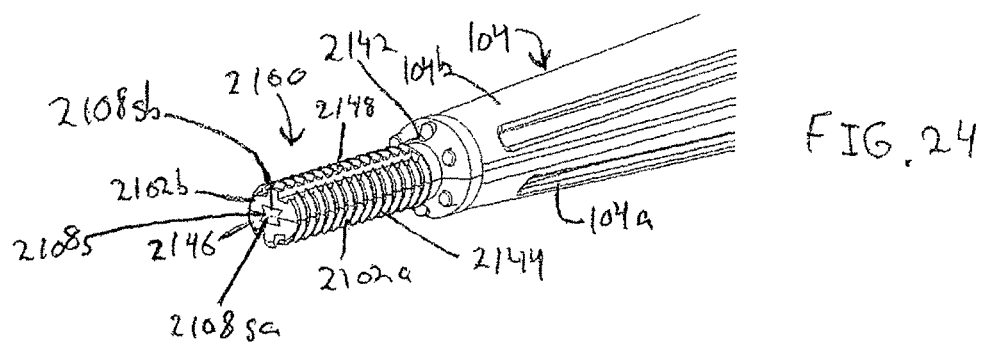
FIG. 24 is a perspective view of an alternative impaling member on a dilator in accordance with the invention.

FIG. 24 shows an alternate impaling member 2100, including a screw 2102, for use with the dilator 104. The screw 2102 is similar to the screw 102, with similar components increased by "2000." The screw 2102 is threaded 2148 in a furrowed pattern, like the screw 102 of FIG. 1A, with alternative threadings also suitable.

Figures 25A, 25B:
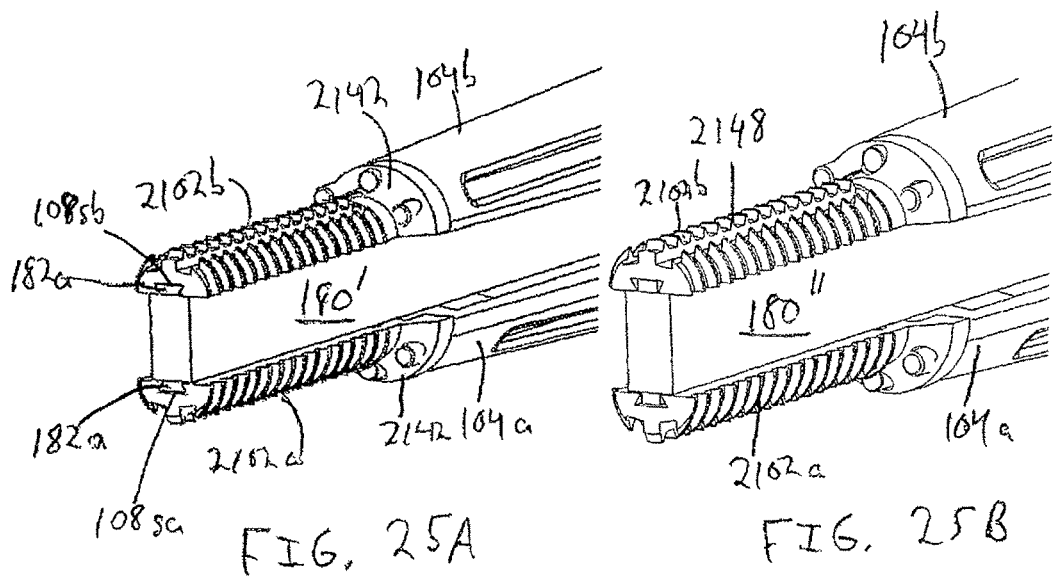
FIGS. 25A and 25B are perspective views showing an exemplary operation of the alternative impaling member of FIG. 24 with its portions being progressively separated.

The difference between the screw 2102 and the screw 102, detailed above, is that the tip 2146 is blunt, and the channel 2108s, formed of dovetailed portions 2108sa and 2108sb, extends to the blunt tip 2046. As a result of the blunt (distal) tip 2146, deployment is by hammering or tapping the apparatus with this impaling member 2100 to the surgical site, for example, the disc space or the sacro iliac joint. The other aspects of dilation and deployment of the screw 2102 to the surgical site are in accordance with that for the apparatus 100, as detailed above. For example, FIGS. 25A and 25B show a progressive dilation of the apparatus and the screw 2102 and dilator 104 thereof, with separator members 180', 180" in accordance with the separator member 180 detailed above and shown in FIGS. 10A and 10B, with separator member 180" of a greater vertical dimension than the separator member 180'.

Figure 26:
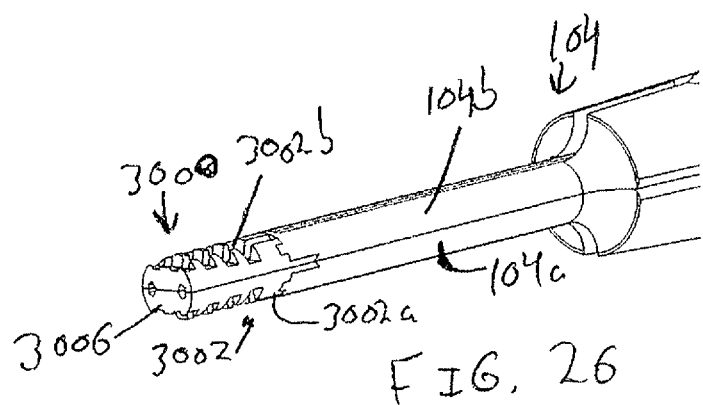
FIG. 26 is a perspective view of another alternative impaling member on a dilator in accordance with the invention.

FIG. 26 illustrates an alternative impaling member 3000, including a screw 3002, for use with the dilator 104, as detailed above. Screw 3002, shown in FIGS. 27A-27D, is similar to the screw 1002, detailed above, and includes a proximal head 3004, similar to screw head 1004 and a blunt distal tip 3006. The head 3004 is designed to attach to the dilator 104, via a stem 3024, which fits in a correspondingly shaped portion of the dilator 104. The shank 3008 is formed of an outward distally tapered core 3010 (taped outward toward the tip 3006). The core 3010 supports threads 3012 in numerous patterns, one such pattern illustrated in FIGS. 27A-27D. The screw 3002, like the screw 1002, is divided into portions 3002a, 3002b, for example, halves, which can be moved apart from each other (in the direction of the double headed arrow 3020) by separator members 180 being extended through the track 108 of the dilator 104 as detailed above for the dilator 104 and screw 102.

Figure 27A:
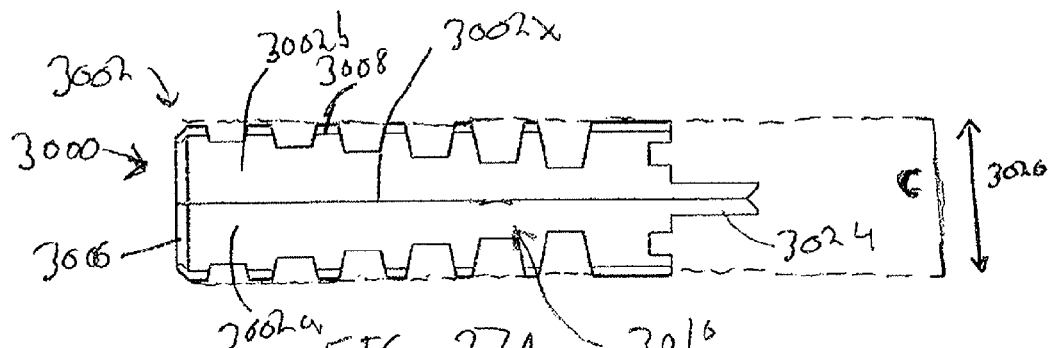
FIG. 27A is a cross sectional view of the alternative impaling member of FIG. 26.
Figure 27B:
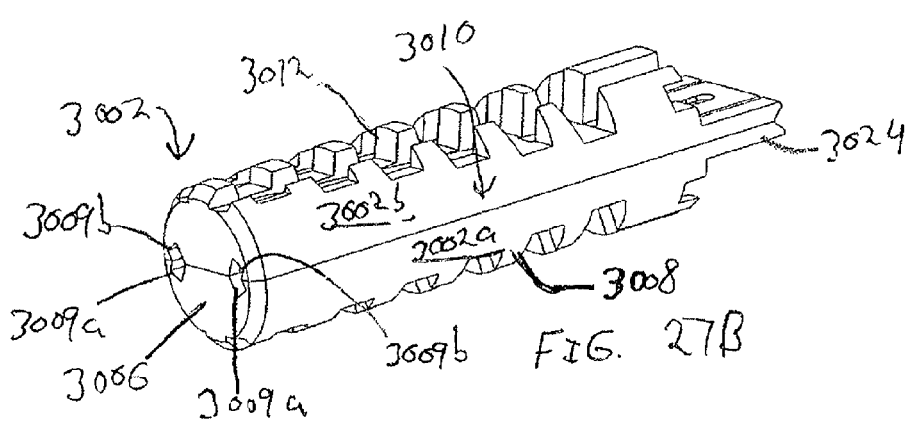
FIG. 27B is a perspective sectional view of the alternative impaling member of FIG. 26.
Figure 27C:
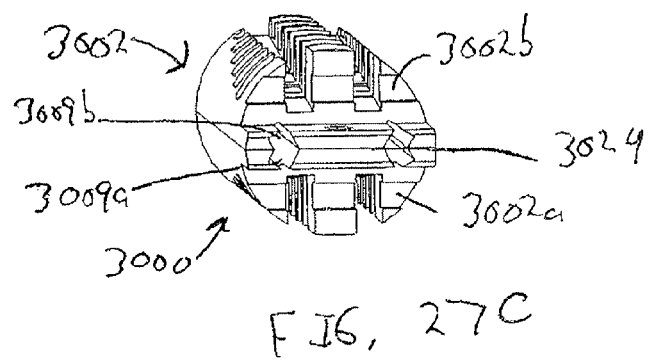
FIG. 27C is a rear view of the alternative impaling member of FIG. 26.
Figure 270:
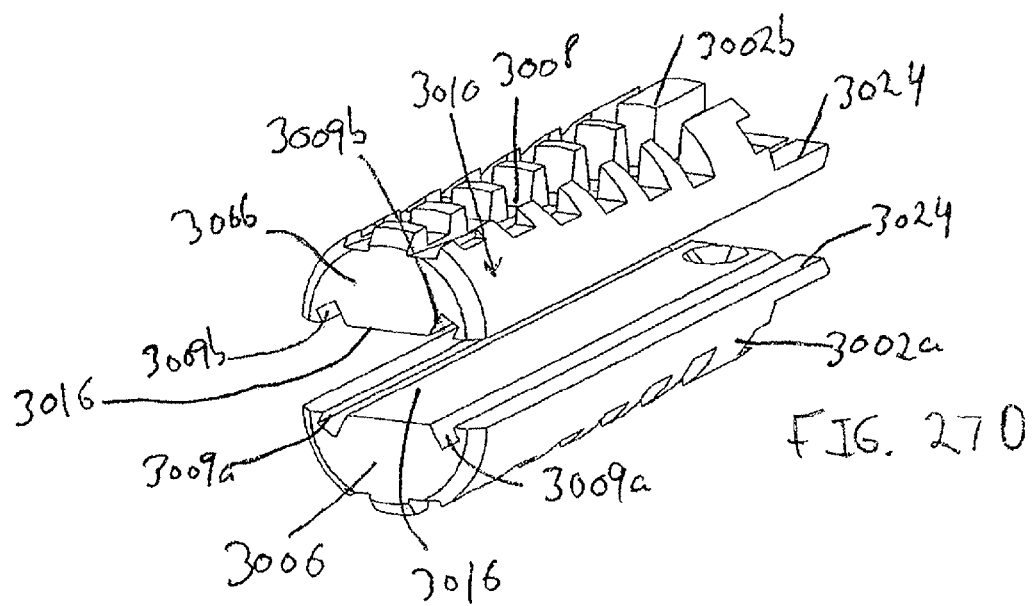
Figure 29B:
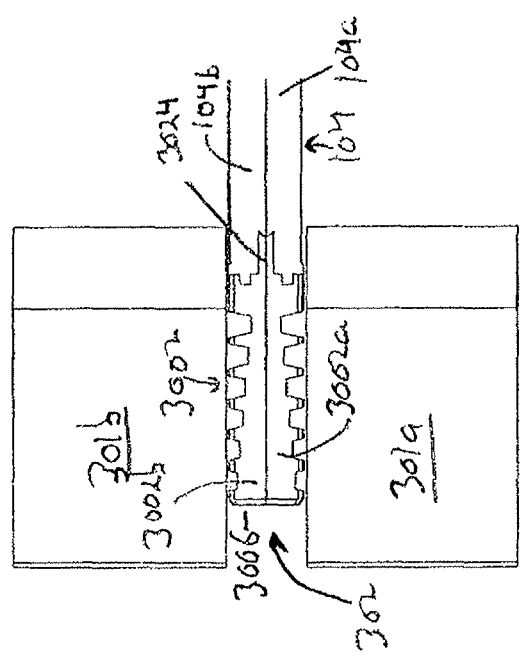

The screw portions 3002a, 3002b are symmetric internally, and typically also externally, as shown, but may be asymmetric depending on the thread pattern. The threads 3012 are such that they are of a constant diameter (c), over the entire core 3010. Unlike the screws 102 and 1002, detailed above, there is not a track portion continuous with the track portions 108d1, 108d2 (FIG. 4A) of the dilator 104. Rather, the screw 3002 is flat (with a floor 3016 as shown) or slightly recessed along its midline 3002x (the slight recessing to form a track for the corresponding portion of the separator member 180 upon separation (dilation or distraction of the screw portions 3002a, 3002b)) with symmetric angled indents 3009a, 3009b in the respective screw portions 3002a, 3002b, to receive the arms 3404a, 3404b of an I-Beam 3400, as shown in FIGS. 27B-27D.

Figure 30:
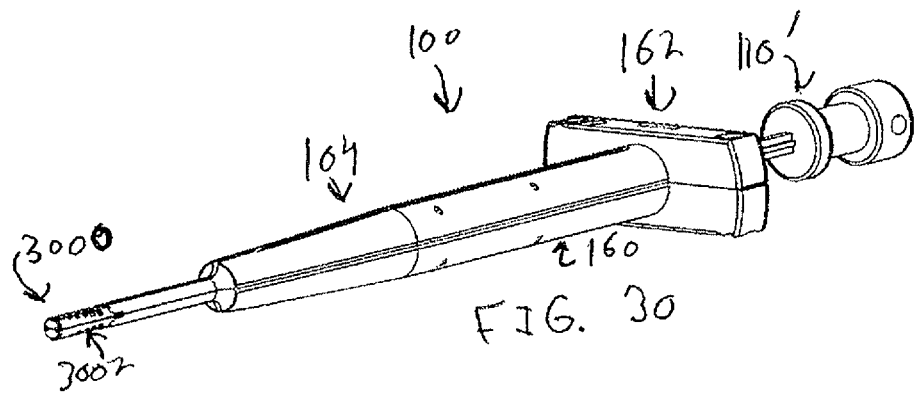
FIG. 30 is a perspective view of the apparatus with the alternative impaling member of FIG. 26 and screwdriver member of FIG. 29 in an exemplary operation.
Figure 29:
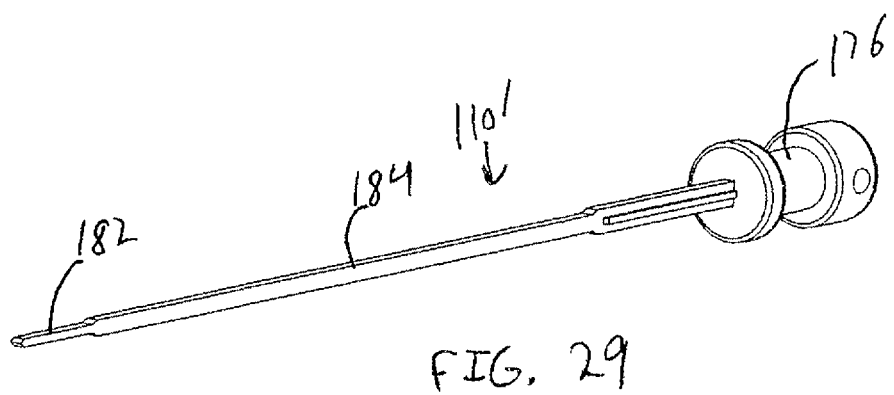
FIG. 29 is a screwdriver member used with the dilator and the alternative impaling member of FIG. 26.

As the screw 3002 has a blunt (distal) tip 3006, deployment is by hammering or tapping the apparatus with this screw 3002 to the surgical site, for example, the disc space 302, between vertebral bodies 301a, 301b (shown progressively in FIGS. 28A, 28B, 28C-1, 28C-2) or the sacro iliac joint. The other aspects of dilation and deployment of the screw 3002 to the surgical site are in accordance with that for the apparatus 100, as detailed above. Additionally, since a track portion in the screw 3002, corresponding to the track portion 108s in the screw 1002 is not present, the screwdriver member 110'(FIG. 29) (similar to screwdriver member 110, shown in FIGS. 9A and 9B and detailed above), upon deployment, extends to the distal end of the dilator 104, positioned no further than track portion 108d1, as shown in FIG. 4B. Accordingly, there is the extra length of the screwdriver member 110 protruding proximally from the dilator 104, as shown in FIG. 30, when compared to the deployment positioning of the screwdriver member 110 in the apparatus 100, as shown in FIG. 12.

Figure 31A:
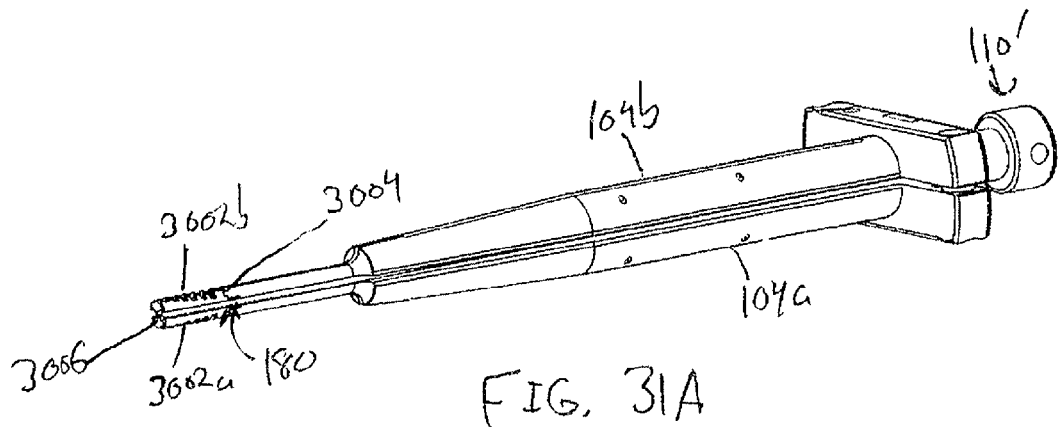
FIGS. 31A-31C are perspective views of the apparatus with the alternative impaling member of FIG. 26 in exemplary progressive separations.
Figure 31B:
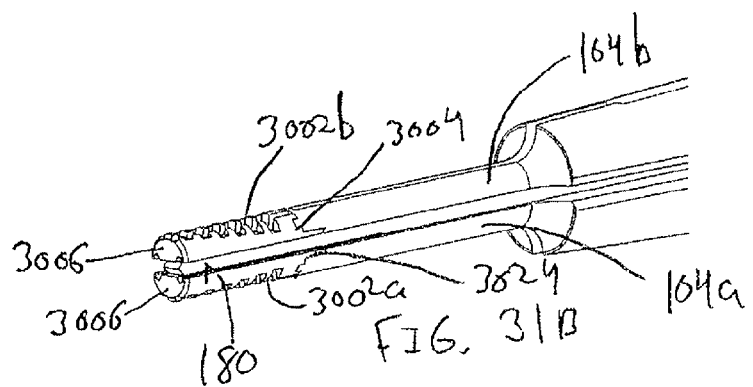
Figure 31C:
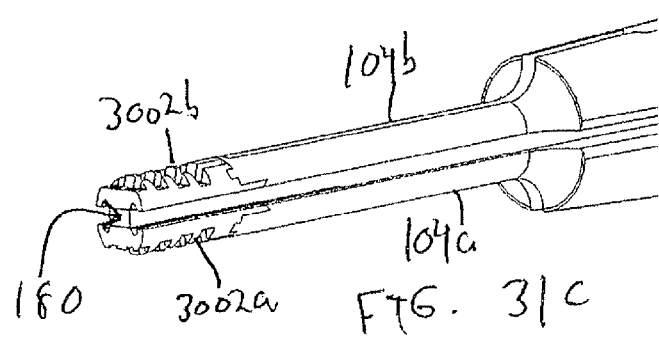

Separation of the screw portions 3002a, 3002b is shown progressively in FIGS. 31A-31C, as the separator member 180 has moved through the track portions 108d2, 108d1 in the dilator 104 and between the screw portions 3002a, 3002b. With the separation of the screw portions 3002a, 3002b complete, and the requisite tissue, e.g., cortical bone impaled, such that the screw portions 3002a, 3002b are attached to this cortical bone (similar to that shown for FIG. 22E and detailed above), the I beam 3400 can be deployed between the screw portions 3002a, 3002b.

Figure 32A:
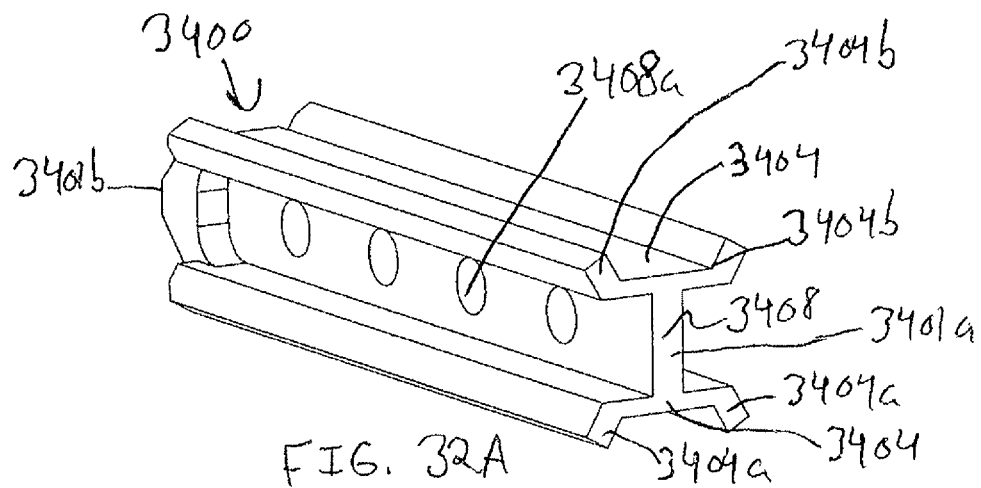
FIG. 32A is a rear perspective view of an I-Beam used with the alternative impaling member of FIG. 26.
Figure 32B:
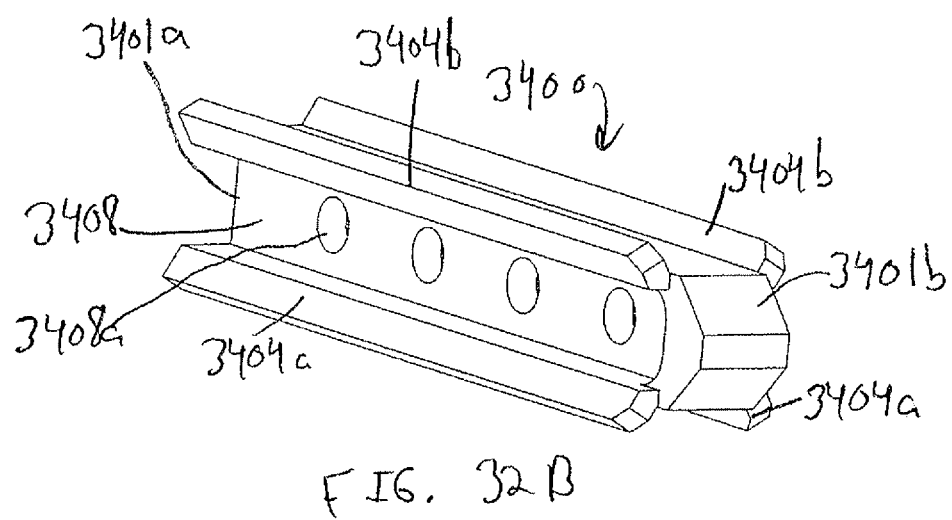
FIG. 32B is a front perspective view of an I-Beam used with the alternative impaling member of FIG. 26.

The I-Beam 3400 is similar to the I-Beam 400 detailed above, except where indicated. As shown in FIGS. 32A and 3213, the I Beam 3400 includes a rear or proximal end

3401*a*, a front or distal end 3401*b* (which orient with respect to the proximal head 3004 and distal end 3006 of the screw 3002), and major portions 3404, joined by a central portion 3408. The major portions 3404 terminate in arms 3404*a*, 3404*b* which slideably engage in the corresponding angled indents 3009*a*, 3009*b*, and include end flanges 3404*a*', 3404*b*' ultimately lock, against shoulders 3011*a*, 3011*b* of the screw 3002, which serve as stop surfaces for the I beam 3400 in the corresponding angled indents 3009*a*, 3009*b* of the screw portions 3002*a*, 3002*b* (FIGS. 33B and 33C). Apertures 3408*a*, may optionally extend through the central portion 3408 of the I-beam 3400.

A successfully deployed I-beam 3400 is shown in FIGS. 33A-33D.

Referring collectively to all of the above embodiments, it should be noted that the split screw device can readily be removed in the event that a surgeon chooses to do so, either immediately post-operatively or if the need arises at a later date. A typical sequence for removing the device includes removal of the spacer beam between the two parts of the device, insertion of the screwdriver or a similar dedicated instrument into the slot of each half-screw separately and rotation of that half-screw through approximately 180 degrees so that the threads, notches and/or protrusions "un-impale" and are turned towards the gap that was previously occupied by the spacer beam. Each half-screw can then be removed axially out of the body.

While C-Beams and I-Beams have been shown with screw fixation, as they are positioned between spread apart screw portions, other supports which would function similarly to the above disclosed C-Beams and I-Beams include, for example, solid, semi-hollow and hollow bars, or members of any other shape which could maintain the separation distance of the screw portions, which are impaled in and attached to the tissue, e.g., bone, typically cortical or compact bone.

It will be appreciated that the above descriptions are intended only to serve as examples, and that many other embodiments are possible within the scope of the present invention as defined in the appended claims.

The invention claimed is:

1. An apparatus for engaging tissue, comprising:
a tissue impaling member including a length spanning from a head of the tissue impaling member to a tip of the tissue impaling member, the tissue impaling member comprising a plurality of portions separable from each other so as to be moved from a closed position to an open position, the plurality of portions defining an interior space when in the closed position, and, the plurality of portions being separated from each other along the entirety of the length when the tissue impaling member is in the open position;
a separator for extending at least partially into the interior space of the plurality of portions and configured for moving in the interior space such that the movement in the interior spaces separates the plurality of portions from the closed position to the open position along the entirety of the length; and,
the portions of the tissue impaling member, when in the closed position, being rotatable into engagement with the tissue, and, the portions of the tissue impaling member, when separated to the open position, are engaged in the tissue and non-rotatable.

2. The apparatus of claim 1, wherein the plurality of portions includes a first portion and a second portion.

3. The apparatus of claim 2, wherein the separator moves the first portion and the second portion outward with respect to each other.

4. The apparatus of claim 3, wherein the tissue impaling member includes a screw divided into portions defining the first portion and the second portion.

5. The apparatus of claim 4, wherein the screw portions are substantially symmetric with respect to each other.

6. The apparatus of claim 5, wherein the screw includes threads configured for impaling the tissue.

7. The apparatus of claim 5, wherein the screw includes threads for impaling bone.

8. The apparatus of claim 5, wherein the screw portions include circumferential projecting ridges.

9. The apparatus of claim 8, wherein the circumferential projecting ridges at least partially define a helical thread.

10. The apparatus of claim 8, wherein the circumferential protruding ridges include cut-out slots defining edges for penetration into tissue.

11. The apparatus of claim 4, wherein the screw includes a substantially conical core, and, threads extending from the substantially conical core, the threads being approximately the same cross sectional diameter.

12. The apparatus of claim 3, wherein movement of the separator causes movement of the first and second portions at least substantially perpendicular to the movement of the separator.

13. The apparatus of claim 3, wherein the separator includes a chamfer in communication with at least one of the first and second portion.

14. The apparatus of claim 1, wherein the portions of the tissue impaling member are adapted for receiving a device when in the open position.

15. The apparatus of claim 14, wherein the device includes a laterally expanding device.

16. The apparatus of claim 1, wherein the tissue impaling member includes an implant.

17. The apparatus of claim 16, wherein the implant is an orthopedic implant.

18. The apparatus of claim 1, wherein the implant includes a bone screw.

19. The apparatus of claim 1, wherein the implant includes a pedicle screw.

20. An apparatus for engaging tissue, comprising:
a tissue impaling member including a length, the entirety of the length extending along all of the apparatus including the tissue impaling member, the tissue impaling member comprising a plurality of portions separable from each other so as to be moved from a closed position to an open position, the plurality of portions defining an interior space when in the closed position, and, the plurality of portions being separated from each other along the entirety of the length when the tissue impaling member is in the open position;
a separator for extending at least partially into the interior space of the plurality of portions and configured for moving in the interior space such that the movement in the interior spaces separates the plurality of portions from the closed position, to the open, position along the entirety of the length; and,
the portions of the tissue impaling member, when in the closed position, being rotatable into engagement with the tissue, and, the portions of the tissue impaling member, when separated to the open position, are engaged in the tissue and non-rotatable.

* * * * *